(12) United States Patent
Zade et al.

(10) Patent No.: US 12,406,760 B2
(45) Date of Patent: Sep. 2, 2025

(54) EXERCISE SAFETY PREDICTION BASED ON PHYSIOLOGICAL CONDITIONS

(71) Applicant: INSULET CORPORATION, Acton, MA (US)

(72) Inventors: Ashutosh Zade, San Diego, CA (US); Joon Bok Lee, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 663 days.

(21) Appl. No.: 17/834,332

(22) Filed: Jun. 7, 2022

(65) Prior Publication Data

US 2022/0392603 A1    Dec. 8, 2022

Related U.S. Application Data

(60) Provisional application No. 63/197,613, filed on Jun. 7, 2021.

(51) Int. Cl.
*G16H 20/30* (2018.01)
*A61B 5/00* (2006.01)
(Continued)

(52) U.S. Cl.
CPC ........... *G16H 20/30* (2018.01); *A61B 5/0004* (2013.01); *A61B 5/0022* (2013.01);
(Continued)

(58) Field of Classification Search
CPC ........ G16H 20/30; G16H 20/17; G16H 40/67; G16H 40/63; A61B 5/0004;
(Continued)

(56) References Cited

U.S. PATENT DOCUMENTS 303,013 A    8/1884   Horton
441,663 A   12/1890   Hofbauer
(Continued)

FOREIGN PATENT DOCUMENTS

AU    2015200834 A1    3/2015
AU    2015301146 A1    3/2017
(Continued)

OTHER PUBLICATIONS

US 5,954,699 A, 09/1999, Jost et al. (withdrawn)
(Continued)

*Primary Examiner* — Eric F Winakur
*Assistant Examiner* — Noah M Healy
(74) *Attorney, Agent, or Firm* — Goodwin Procter LLP

(57) ABSTRACT

Described are techniques, processes, devices, computer-readable media that enable provision of an indication of whether it is safe for a person with diabetes to participate in exercise while using a wearable drug delivery system. A processor may receive or obtain physiological data related to a condition of a wearer of the wearable drug delivery system and by evaluating an exercise model that uses inputs related to the physiological data to make the determination of whether it is safe to exercise and output an exercise safety signal. Modifications to the wearer's medication treatment plan and other actions may be based on an outputted exercise safety signal.

20 Claims, 7 Drawing Sheets

(51) Int. Cl.
 *A61B 5/145* (2006.01)
 *A61M 5/172* (2006.01)
 *G16H 20/17* (2018.01)

(52) U.S. Cl.
 CPC ........ *A61B 5/14532* (2013.01); *A61B 5/7267* (2013.01); *A61B 5/7275* (2013.01); *A61B 5/743* (2013.01); *A61B 5/7475* (2013.01); *A61M 5/1723* (2013.01); *G16H 20/17* (2018.01)

(58) Field of Classification Search
 CPC . A61B 5/14532; A61B 5/7267; A61B 5/7275; A61B 5/4839; A61B 5/1118; A61B 5/11; A61B 5/746; A61B 5/0022; A61B 5/7264; A61B 5/7475; A61M 5/1723; A61M 2230/201; A61M 2205/50; A61M 2005/14208; A61M 2205/18
 See application file for complete search history.

(56) References Cited

U.S. PATENT DOCUMENTS

| | | |
|---|---|---|
| 955,911 A | 4/1910 | Saegmuller |
| 1,441,508 A | 1/1923 | Marius |
| 2,797,149 A | 6/1957 | Skeggs |
| 2,987,214 A | 6/1961 | Radack |
| 3,579,805 A | 5/1971 | Kast |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,206,401 A | 6/1980 | Meyer |
| 4,245,634 A | 1/1981 | Albisser et al. |
| 4,277,226 A | 7/1981 | Archibald |
| 4,307,713 A | 12/1981 | Galkin et al. |
| 4,368,980 A | 1/1983 | Aldred et al. |
| 4,373,527 A | 2/1983 | Fischell |
| 4,398,542 A | 8/1983 | Cunningham et al. |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,560,979 A | 12/1985 | Rosskopf |
| 4,573,968 A | 3/1986 | Parker |
| 4,587,850 A | 5/1986 | Moser |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,833,088 A | 5/1989 | Desimone et al. |
| 4,836,752 A | 6/1989 | Burkett |
| 4,850,954 A | 7/1989 | Charvin |
| 4,854,170 A | 8/1989 | Brimhall et al. |
| 4,882,600 A | 11/1989 | Van de Moere |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,961,055 A | 10/1990 | Habib et al. |
| 4,973,998 A | 11/1990 | Gates |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,045,871 A | 9/1991 | Reinholdson |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,232,668 A | 8/1993 | Grant et al. |
| 5,237,993 A | 8/1993 | Skrabal |
| 5,239,326 A | 8/1993 | Takai |
| 5,244,459 A | 9/1993 | Hill |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,452,033 A | 9/1995 | Balling et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,563,584 A | 10/1996 | Rader et al. |
| 5,569,186 A | 10/1996 | Lord et al. |
| 5,576,781 A | 11/1996 | Deleeuw |
| 5,584,813 A | 12/1996 | Livingston et al. |
| 5,585,733 A | 12/1996 | Paglione |
| 5,586,553 A | 12/1996 | Halili et al. |
| 5,609,572 A | 3/1997 | Lang |
| 5,647,853 A | 7/1997 | Feldmann et al. |
| 5,660,163 A | 8/1997 | Schulman et al. |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,726,404 A | 3/1998 | Brody |
| 5,726,751 A | 3/1998 | Altendorf et al. |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,785,681 A | 7/1998 | Indravudh et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,830,999 A | 11/1998 | Dunn |

(56) References Cited

U.S. PATENT DOCUMENTS

| | | |
|---|---|---|
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,867,688 A | 2/1999 | Simmon et al. |
| 5,871,470 A | 2/1999 | McWha |
| 5,879,310 A | 3/1999 | Sopp et al. |
| 5,899,882 A | 5/1999 | Waksman et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,995,236 A | 11/1999 | Roth et al. |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,181 A | 11/2000 | Schumacher |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,171,264 B1 | 1/2001 | Bader |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,381,029 B1 | 4/2002 | Tipirneni |
| 6,402,689 B1 | 6/2002 | Scarantino et al. |
| 6,418,332 B1 | 7/2002 | Mastrototaro et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,514,460 B1 | 2/2003 | Fendrock |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,685,452 B2 | 2/2004 | Christiansen et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,768,319 B2 | 7/2004 | Wang |
| 6,768,425 B2 | 7/2004 | Flaherty et al. |
| 6,780,156 B2 | 8/2004 | Haueter et al. |
| 6,810,290 B2 | 10/2004 | Lebel et al. |
| 6,830,558 B2 | 12/2004 | Flaherty et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,137,964 B2 | 11/2006 | Flaherty |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,182,726 B2 | 2/2007 | Williams et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,073 B2 | 12/2007 | Raynal-Olive et al. |
| 7,303,549 B2 | 12/2007 | Flaherty et al. |

(56) References Cited

U.S. PATENT DOCUMENTS

| | | |
|---|---|---|
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Ebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,731,900 B2 | 6/2010 | Haar et al. |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,842,241 B2 | 11/2010 | Arbogast et al. |
| 7,846,385 B2 | 12/2010 | Arbogast et al. |
| 7,846,386 B2 | 12/2010 | Arbogast et al. |
| 7,846,387 B2 | 12/2010 | Arbogast et al. |
| 7,846,388 B2 | 12/2010 | Arbogast et al. |
| 7,867,446 B2 | 1/2011 | Arbogast et al. |
| 7,897,107 B2 | 3/2011 | Arbogast et al. |
| 7,914,742 B2 | 3/2011 | Arbogast et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,003,052 B2 | 8/2011 | Sacherer |
| 8,056,719 B2 | 11/2011 | Porret et al. |
| 8,080,205 B2 | 12/2011 | Arbogast et al. |
| 8,105,282 B2 | 1/2012 | Susi et al. |
| 8,221,345 B2 | 7/2012 | Blomquist |
| 8,251,907 B2 | 8/2012 | Sterling et al. |
| 8,285,487 B2 | 10/2012 | Bergstrom et al. |
| 8,431,408 B2 | 4/2013 | Lewis et al. |
| 8,449,524 B2 | 5/2013 | Braig et al. |
| 8,452,359 B2 | 5/2013 | Rebec et al. |
| 8,454,557 B1 | 6/2013 | Qi et al. |
| 8,454,576 B2 | 6/2013 | Mastrototaro et al. |
| 8,461,561 B2 | 6/2013 | Freeman et al. |
| 8,465,977 B2 | 6/2013 | Joseph et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,701,264 B2 | 4/2014 | Martinson |
| 8,727,117 B2 | 5/2014 | Maasarani |
| 8,765,482 B2 | 7/2014 | Joseph et al. |
| 8,810,394 B2 | 8/2014 | Kalpin |
| 8,894,262 B2 | 11/2014 | Celentano et al. |
| 9,005,166 B2 | 4/2015 | Uber, III et al. |
| 9,061,097 B2 | 6/2015 | Holt et al. |
| 9,171,343 B1 | 10/2015 | Fischell et al. |
| 9,233,204 B2 | 1/2016 | Booth et al. |
| 9,248,229 B2 | 2/2016 | Devouassoux et al. |
| 9,265,877 B2 | 2/2016 | Mcarthur et al. |
| 9,427,710 B2 | 8/2016 | Jansen |
| 9,486,571 B2 | 11/2016 | Rosinko |
| 9,572,926 B2 | 2/2017 | Cabiri |
| 9,579,456 B2 | 2/2017 | Budiman et al. |
| 9,598,195 B2 | 3/2017 | Deutschle et al. |
| 9,743,224 B2 | 8/2017 | San Vicente et al. |
| 9,814,832 B2 | 11/2017 | Agard et al. |
| 9,862,519 B2 | 1/2018 | Deutschle et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,046,114 B1 | 8/2018 | Biederman et al. |
| RE47,100 E | 10/2018 | Smith et al. |
| 10,086,131 B2 | 10/2018 | Okihara |
| 10,248,839 B2 | 4/2019 | Levy et al. |
| 10,335,464 B1 | 7/2019 | Michelich et al. |
| 10,342,926 B2 | 7/2019 | Nazzaro et al. |
| 10,441,717 B2 | 10/2019 | Schmid et al. |
| 10,583,250 B2 | 3/2020 | Mazlish et al. |
| 10,661,012 B2 | 5/2020 | Nazzaro et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0032374 A1 | 3/2002 | Holker et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0161307 A1 | 10/2002 | Yu et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0073952 A1 | 4/2003 | Flaherty et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0010507 A1 | 1/2004 | Bellew |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0085215 A1 | 5/2004 | Moberg et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0009126 A1 | 1/2005 | Andrews et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0055242 A1 | 3/2005 | Bello et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0125162 A1 | 6/2005 | Hajizadeh et al. |
| 2005/0137573 A1 | 6/2005 | McLaughlin |

(56) References Cited

U.S. PATENT DOCUMENTS

| | | |
|---|---|---|
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0201897 A1 | 9/2005 | Zimmer et al. |
| 2005/0203360 A1 | 9/2005 | Brauker et al. |
| 2005/0203461 A1 | 9/2005 | Flaherty et al. |
| 2005/0232815 A1 | 10/2005 | Ruhl et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277164 A1 | 12/2005 | Drucker et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0086909 A1 | 4/2006 | Schaber |
| 2006/0092569 A1 | 5/2006 | Che et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0264926 A1 | 11/2006 | Kochamba |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0027370 A1 | 2/2007 | Brauker et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0078784 A1 | 4/2007 | Donovan et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0179885 A1 | 8/2007 | Bird et al. |
| 2007/0191716 A1 | 8/2007 | Goldberger et al. |
| 2007/0191770 A1 | 8/2007 | Moberg et al. |
| 2007/0197163 A1 | 8/2007 | Robertson |
| 2007/0225675 A1 | 9/2007 | Robinson et al. |
| 2007/0233051 A1 | 10/2007 | Hohl et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0004515 A1 | 1/2008 | Jennewine |
| 2008/0027371 A1 | 1/2008 | Higuchi et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0077081 A1 | 3/2008 | Mounce et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0173073 A1 | 7/2008 | Downie et al. |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0255438 A1 | 10/2008 | Saidara et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0281290 A1 | 11/2008 | Yodfat et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0048556 A1 | 2/2009 | Durand |
| 2009/0054753 A1 | 2/2009 | Robinson et al. |
| 2009/0062767 A1 | 3/2009 | Van Antwerp et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0112769 A1 | 4/2009 | Dicks et al. |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0177142 A1 | 7/2009 | Blomquist et al. |
| 2009/0198350 A1 | 8/2009 | Thiele |
| 2009/0204078 A1 | 8/2009 | Mitchell et al. |
| 2009/0221890 A1 | 9/2009 | Saffer et al. |
| 2009/0228214 A1 | 9/2009 | Say et al. |
| 2009/0254041 A1 | 10/2009 | Krag et al. |
| 2009/0282947 A1 | 11/2009 | Powell |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0076275 A1 | 3/2010 | Chu et al. |
| 2010/0094251 A1 | 4/2010 | Estes |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0168683 A1 | 7/2010 | Cabiri |
| 2010/0174228 A1 | 7/2010 | Buckingham et al. |
| 2010/0185175 A1 | 7/2010 | Kamen et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0286997 A1 | 11/2010 | Srinivasan |
| 2010/0295686 A1 | 11/2010 | Sloan et al. |
| 2010/0298765 A1 | 11/2010 | Budiman et al. |
| 2010/0317951 A1 | 12/2010 | Rutkowski et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0071765 A1 | 3/2011 | Yodfat et al. |
| 2011/0124996 A1 | 5/2011 | Reinke et al. |
| 2011/0142688 A1 | 6/2011 | Chappel et al. |
| 2011/0144586 A1 | 6/2011 | Michaud et al. |
| 2011/0152658 A1 | 6/2011 | Peyser et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0193704 A1 | 8/2011 | Harper et al. |
| 2011/0202005 A1 | 8/2011 | Yodfat et al. |
| 2011/0213306 A1 | 9/2011 | Hanson et al. |
| 2011/0218495 A1 | 9/2011 | Remebe |
| 2011/0225024 A1 | 9/2011 | Seyer et al. |
| 2011/0230833 A1 | 9/2011 | Andman et al. |

(56) References Cited

U.S. PATENT DOCUMENTS

| | | |
|---|---|---|
| 2011/0246235 A1 | 10/2011 | Powell et al. |
| 2011/0251509 A1 | 10/2011 | Beyhan et al. |
| 2011/0289497 A1 | 11/2011 | Kiaie et al. |
| 2011/0313680 A1 | 12/2011 | Doyle, III |
| 2011/0316562 A1 | 12/2011 | Cefai et al. |
| 2012/0003935 A1 | 1/2012 | Ydon et al. |
| 2012/0010594 A1 | 1/2012 | Holt et al. |
| 2012/0029941 A1 | 2/2012 | Malave et al. |
| 2012/0030393 A1 | 2/2012 | Ganesh et al. |
| 2012/0050046 A1 | 3/2012 | Satorius et al. |
| 2012/0053556 A1 | 3/2012 | Lee |
| 2012/0054841 A1 | 3/2012 | Schultz et al. |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0095316 A1 | 4/2012 | Lewis et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0153936 A1 | 6/2012 | Romani et al. |
| 2012/0182939 A1 | 7/2012 | Rajan et al. |
| 2012/0184909 A1 | 7/2012 | Gyrn |
| 2012/0190955 A1 | 7/2012 | Rao et al. |
| 2012/0201048 A1 | 8/2012 | Prais |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0265166 A1 | 10/2012 | Yodfat |
| 2012/0271655 A1 | 10/2012 | Knobel et al. |
| 2012/0277667 A1 | 11/2012 | Yodat et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0030841 A1 | 1/2013 | Bergstrom et al. |
| 2013/0036100 A1 | 2/2013 | Nagpal et al. |
| 2013/0060194 A1 | 3/2013 | Rostein |
| 2013/0080832 A1 | 3/2013 | Dean et al. |
| 2013/0138452 A1 | 5/2013 | Cork et al. |
| 2013/0158503 A1 | 6/2013 | Kanderian, Jr. et al. |
| 2013/0173473 A1 | 7/2013 | Birtwhistle et al. |
| 2013/0178791 A1 | 7/2013 | Javitt |
| 2013/0204130 A1 | 8/2013 | Mcarthur et al. |
| 2013/0231642 A1 | 9/2013 | Doyle et al. |
| 2013/0245545 A1 | 9/2013 | Arnold et al. |
| 2013/0253472 A1 | 9/2013 | Cabiri |
| 2013/0261406 A1 | 10/2013 | Rebec et al. |
| 2013/0274576 A1 | 10/2013 | Amirouche et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0012119 A1 | 1/2014 | Geaghan et al. |
| 2014/0054883 A1 | 2/2014 | Lanigan et al. |
| 2014/0066886 A1 | 3/2014 | Roy et al. |
| 2014/0074033 A1 | 3/2014 | Sonderegger et al. |
| 2014/0078263 A1 | 3/2014 | Kim |
| 2014/0114277 A1 | 4/2014 | Eggert et al. |
| 2014/0121635 A1 | 5/2014 | Hayter |
| 2014/0128839 A1 | 5/2014 | Dilanni et al. |
| 2014/0131199 A1 | 5/2014 | Simmons et al. |
| 2014/0135880 A1 | 5/2014 | Baumgartner et al. |
| 2014/0146202 A1 | 5/2014 | Boss et al. |
| 2014/0148784 A1 | 5/2014 | Anderson et al. |
| 2014/0163664 A1 | 6/2014 | Goldsmith |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0254170 A1 | 9/2014 | Celentano et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0296787 A1 | 10/2014 | Agard et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0038898 A1 | 2/2015 | Palmer et al. |
| 2015/0057913 A1 | 2/2015 | Benhammou |
| 2015/0119666 A1 | 4/2015 | Brister et al. |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0283335 A1 | 10/2015 | Lin |
| 2015/0290391 A1 | 10/2015 | Schmid et al. |
| 2015/0306314 A1 | 10/2015 | Doyle et al. |
| 2015/0338349 A1 | 11/2015 | Carter et al. |
| 2015/0351671 A1 | 12/2015 | Vanslyke et al. |
| 2015/0361154 A1 | 12/2015 | Jowett et al. |
| 2015/0366945 A1 | 12/2015 | Greene |
| 2016/0015891 A1 | 1/2016 | Papiorek |
| 2016/0022905 A1 | 1/2016 | Nagar et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0058941 A1 | 3/2016 | Wu et al. |
| 2016/0082187 A1 | 3/2016 | Schaible et al. |
| 2016/0089494 A1 | 3/2016 | Guerrini |
| 2016/0135747 A1 | 5/2016 | Frey et al. |
| 2016/0175520 A1 | 6/2016 | Palerm et al. |
| 2016/0184517 A1 | 6/2016 | Baek et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0310665 A1 | 10/2016 | Hwang et al. |
| 2016/0331310 A1 | 11/2016 | Kovatchev |
| 2016/0339172 A1 | 11/2016 | Michaud et al. |
| 2016/0354543 A1 | 12/2016 | Cinar et al. |
| 2017/0028132 A1 | 2/2017 | Cronenberg et al. |
| 2017/0049386 A1 | 2/2017 | Abraham et al. |
| 2017/0106138 A1 | 4/2017 | Cabiri |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189270 A1 | 7/2017 | Nazzaro et al. |
| 2017/0189625 A1 | 7/2017 | Cirillo et al. |
| 2017/0214584 A1 | 7/2017 | Kanojia et al. |
| 2017/0234858 A1 | 8/2017 | Depa et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348479 A1 | 12/2017 | Choate et al. |
| 2017/0348482 A1 | 12/2017 | Duke et al. |
| 2017/0354785 A1 | 12/2017 | Gazeley et al. |
| 2018/0015274 A1 | 1/2018 | Haury et al. |
| 2018/0036495 A1 | 2/2018 | Searle et al. |
| 2018/0040255 A1 | 2/2018 | Freeman et al. |
| 2018/0055452 A1 | 3/2018 | Breton |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |

(56) References Cited

U.S. PATENT DOCUMENTS

| | | | |
|---|---|---|---|
| 2018/0207357 A1 | 7/2018 | John | |
| 2018/0236173 A1 | 8/2018 | Mccaffrey et al. | |
| 2018/0256815 A1 | 9/2018 | Nazzaro | |
| 2018/0277253 A1 | 9/2018 | Gondhalekar et al. | |
| 2018/0280609 A1 | 10/2018 | Nishimura et al. | |
| 2018/0289891 A1 | 10/2018 | Finan et al. | |
| 2018/0296757 A1 | 10/2018 | Finan et al. | |
| 2018/0307515 A1 | 10/2018 | Meller et al. | |
| 2018/0342317 A1 | 11/2018 | Skirble et al. | |
| 2018/0369479 A1 | 12/2018 | Hayter et al. | |
| 2019/0022317 A1 | 1/2019 | Uddin et al. | |
| 2019/0076600 A1 | 3/2019 | Grosman et al. | |
| 2019/0091404 A1 | 3/2019 | Nazzaro et al. | |
| 2019/0132801 A1 | 5/2019 | Kamath et al. | |
| 2019/0167895 A1 | 6/2019 | Dechellette et al. | |
| 2019/0240403 A1 | 8/2019 | Palerm et al. | |
| 2019/0240417 A1 | 8/2019 | Hostettler et al. | |
| 2019/0290844 A1 | 9/2019 | Monirabbasi et al. | |
| 2019/0321545 A1 | 10/2019 | Saint | |
| 2019/0336683 A1 | 11/2019 | O'Connor et al. | |
| 2019/0336684 A1 | 11/2019 | O'Connor et al. | |
| 2019/0348157 A1 | 11/2019 | Booth et al. | |
| 2020/0046268 A1 | 2/2020 | Patek et al. | |
| 2020/0101222 A1 | 4/2020 | Intereur et al. | |
| 2020/0101223 A1 | 4/2020 | Lintereur et al. | |
| 2020/0101225 A1 | 4/2020 | O'Connor et al. | |
| 2020/0197605 A1 | 6/2020 | Haidar | |
| 2020/0219625 A1 | 7/2020 | Kahlbaugh | |
| 2020/0261643 A1 | 8/2020 | Boyaval et al. | |
| 2020/0342974 A1 | 10/2020 | Chen et al. | |
| 2021/0050085 A1 | 2/2021 | Hayter et al. | |
| 2021/0098105 A1 | 4/2021 | Lee et al. | |
| 2021/0256872 A1* | 8/2021 | Matsumoto | G16H 50/20 |
| 2022/0023536 A1 | 1/2022 | Graham et al. | |

FOREIGN PATENT DOCUMENTS

| | | | |
|---|---|---|---|
| CA | 2863379 A1 | 8/2013 |
| CN | 1297140 A | 5/2001 |
| CN | 201134101 Y | 10/2008 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 1762263 A1 | 3/2007 |
| EP | 1839694 A1 | 10/2007 |
| EP | 1852703 A1 | 11/2007 |
| EP | 2099384 A1 | 9/2009 |
| EP | 2139382 A1 | 1/2010 |
| EP | 2353628 A2 | 8/2011 |
| EP | 2397181 A1 | 12/2011 |
| EP | 2666520 A1 | 11/2013 |
| EP | 2695573 A2 | 2/2014 |
| EP | 1874390 B1 | 10/2014 |
| EP | 2830499 A1 | 2/2015 |
| EP | 2943149 A1 | 11/2015 |
| EP | 3068290 A1 | 9/2016 |
| EP | 3135965 A1 | 3/2017 |
| EP | 3177344 A1 | 6/2017 |
| EP | 3187201 A1 | 7/2017 |
| EP | 3314548 A1 | 5/2018 |
| EP | 3000497 A1 | 1/2019 |
| EP | 1571582 B1 | 4/2019 |
| EP | 2897071 B1 | 5/2019 |
| EP | 3598942 A1 | 1/2020 |
| EP | 3607985 A1 | 2/2020 |
| ES | 2559866 T3 | 2/2016 |
| FR | 2096275 A5 | 2/1972 |
| GB | 357139 A | 9/1931 |
| GB | 810488 A | 3/1959 |
| GB | 1401588 A | 7/1975 |
| GB | 2176595 A | 12/1986 |
| GB | 2443260 A | 4/2008 |
| GB | 2443261 A | 4/2008 |
| GB | 2461086 A | 12/2009 |
| GB | 2495014 A | 3/2013 |
| GB | 2524717 A | 10/2015 |
| GB | 2525149 A | 10/2015 |
| JP | 51125993 A | 11/1976 |
| JP | 02131777 A | 5/1990 |
| JP | 2001190659 A | 7/2001 |
| JP | 2003154190 A | 5/2003 |
| JP | 2007144141 A1 | 6/2007 |
| JP | 2004283378 A | 10/2007 |
| JP | 2007307359 A | 11/2007 |
| JP | 2008242502 A | 10/2008 |
| JP | 2009523535 A | 6/2009 |
| JP | 2012210441 A | 11/2012 |
| JP | 2017525451 A | 9/2017 |
| JP | 2018153569 A | 10/2018 |
| JP | 2019525276 A | 9/2019 |
| NO | 2008024814 A2 | 2/2008 |
| TW | 200740148 A | 10/2007 |
| TW | M452390 U | 5/2013 |
| WO | 9800193 A1 | 1/1998 |
| WO | 9801071 A1 | 1/1998 |
| WO | 9819145 A1 | 5/1998 |
| WO | 9824495 A1 | 6/1998 |
| WO | 9841267 A1 | 9/1998 |
| WO | 9956803 A1 | 11/1999 |
| WO | 0010628 A2 | 3/2000 |
| WO | 0013580 A1 | 3/2000 |
| WO | 0019887 A1 | 4/2000 |
| WO | 0030705 A1 | 6/2000 |
| WO | 200032258 A1 | 6/2000 |
| WO | 0061215 A1 | 10/2000 |
| WO | 0078210 A1 | 12/2000 |
| WO | 0172354 A2 | 10/2001 |
| WO | 2002015954 A1 | 2/2002 |
| WO | 2002043866 A2 | 6/2002 |
| WO | 2002082990 A1 | 10/2002 |
| WO | 2003016882 A1 | 2/2003 |
| WO | 2003039362 A1 | 5/2003 |
| WO | 2003045233 A1 | 6/2003 |
| WO | 2004043250 A1 | 5/2004 |
| WO | 2005110601 A1 | 5/2004 |
| WO | 2004092715 A1 | 10/2004 |
| WO | 2005031631 A2 | 4/2005 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2006060668 A2 | 6/2006 |
| WO | 2007064835 A2 | 6/2007 |
| WO | 2007078937 A1 | 7/2007 |
| WO | 2007084214 A1 | 7/2007 |
| WO | 2007092618 A2 | 8/2007 |
| WO | 2007112034 A2 | 10/2007 |
| WO | 2008024810 A2 | 2/2008 |
| WO | 2008029403 A1 | 3/2008 |
| WO | 2008133702 A1 | 11/2008 |
| WO | 2009023634 A2 | 2/2009 |
| WO | 2009032399 A1 | 3/2009 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010025433 A1 | 3/2010 |
| WO | 2010053702 A1 | 5/2010 |
| WO | 2010078434 A2 | 7/2010 |
| WO | 2010132077 A1 | 11/2010 |
| WO | 2010138848 A1 | 12/2010 |
| WO | 2010146579 A1 | 12/2010 |
| WO | 2010147659 A2 | 12/2010 |
| WO | 2011012465 A1 | 2/2011 |
| WO | 2011095483 A1 | 8/2011 |
| WO | 2011133823 A1 | 10/2011 |
| WO | 2012045667 A2 | 4/2012 |
| WO | 2012108959 A1 | 8/2012 |
| WO | 2012134588 A1 | 10/2012 |

(56) References Cited

FOREIGN PATENT DOCUMENTS

| | | |
|---|---|---|
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 2013149186 A1 | 10/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014136105 A1 | 9/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2015187793 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2016181384 A2 | 11/2016 |
| WO | 2017004278 A1 | 1/2017 |
| WO | 2017089289 A1 | 6/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019043702 A1 | 3/2019 |
| WO | 2019077482 A1 | 4/2019 |
| WO | 2019094440 A1 | 5/2019 |
| WO | 2019195521 A1 | 10/2019 |
| WO | 2019213493 A1 | 11/2019 |
| WO | 2019246381 A1 | 12/2019 |
| WO | 2020081393 A1 | 4/2020 |
| WO | 2020124058 A1 | 6/2020 |
| WO | 2021011738 A1 | 1/2021 |

OTHER PUBLICATIONS

Breton et al., "Continuous Glucose Monitoring and Insulin Informed Advisory System with Automated Titration and Dosing of Insulin Reduces Glucose Variability in Type 1 Diabetes Mellitus", Diabetes Technology & Therapeutics, vol. 20, No. 8, 2018. (Year: 2018).*
European Search Report for the European Patent Application No. EP03743667, dated Jul. 22, 2008.
International Search Report and Written Opinion mailed Sep. 9, 2016, issued in PCT Patent Application No. PCT/US2016/037189, 12 pages.
Preliminary Report on Patentability mailed Dec. 21, 2017, issued in PCT Patent Application No. PCT/US2016/037189.
U.K. Intellectual Property Office, GB Application No. GB 1401587.9, "Search Report under Section 17(5)" Aug. 11, 2015, 1 page.
International Search Report and Written Opinion for PCT Application No. PCT/GB2015/050247, May 8, 2015, 14 pages.
Extended Search Report mailed Nov. 24, 2017, issued in European Patent Application No. 15779465.2, 10 pages.
International Search Report and Written Opinion for PCT Application No. PCT/US15/26875, mailed Jan. 18, 2016, 10 pages.
U.K. Intellectual Property Office, GB Application No. GB 1401588.7, "Search Report under Section 17(5)" Aug. 17, 2015, 1 page.
U.K. Intellectual Property Office, GB Application No. GB 1401589.5, "Search Report under Section 17" Jul. 27, 2015, 1 page.
International Search Report and Written Opinion for PCT Application No. PCT/GB2015/050250, May 7, 2015, 9 pages.
3GPP TS 23.003 V10.0.0.0 Numbering, addressing and identification. Dec. 2010.
International Search Report and Written Opinion for PCT Application No. PCT/GB2015/050251, Jun. 12, 2015, 9 bages.
European Search Report for the European Patent Application No. EP19194241, dated Oct. 22, 2019, 6 pages.
International Preliminary Report on Patentability for PCT/US2017/061095, issued on May 14, 2019, 6 pages.
International Search Report and Written Opinion for PCT/US18/52468, mailed on Feb. 26, 2019, 16 pages.
International Search Report and Written Opinion for PCT/US2017/061095, mailed on Feb. 20, 2018, 8 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A "Microbial Contamination Of Haemodialysis Catheter Connections" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al., "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010.

(56) References Cited

OTHER PUBLICATIONS

International Search Report and Written Opinion in PCT/US2008/079641 dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech, vol. Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
International Preliminary Report on Patentability for the International Patent Application No. PCT/US2019/042160, mailed Jan. 28, 2021, 12 pages.
International Search Report and Written Opinion for the International Patent Application No. PCT/US2021/047695, mailed Jan. 31, 2022, 26 pages.
International Search Report and Written Opinion for the International Patent Application No. PCT/US21/064056, mailed Apr. 4, 2022, 12 pages.
Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.
International Search Report and Written Opinion for the International Patent Application No. PCT/US22/018700, mailed Jun. 7, 2022, 13 pages.
Legacy Med Search, Insulet Enrolls First Patients in Clinical Trial for Omnipod, Sep. 16, 2016, available at URL: https://legacymedsearch.com/insulet-enrolls-first-patients-in-clinical-trial-for-omnipod-artificial-pancreas-system/.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.

(56) References Cited

OTHER PUBLICATIONS

International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator -in silicoevaluation under intra-day variability", Computer Methods and Programs in Biomedicine, Elsevier, Amsterdam, Nl, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand col. line 16- line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G .; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for International Patent Application No. PCT/US2022/029012, mailed Aug. 19, 2022, 12 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

(56) References Cited

OTHER PUBLICATIONS

"Read NFC Tags with an iPHone App on iOS 11", GoToTags, Sep. 11, 2017, web <https://gototags.com/blog/read-hfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.
International Search Report and Written Opinion for the International Patent Application No. PCT/US2021/047690, mailed Jan. 14, 2022, 13 pages.
International Search Report and Written Opinion for the International Patent Application No. PCT/US2022/055745, mailed Feb. 14, 2022, 13 pages.
International Search Report and Written Opinion for the International Patent Application No. PCT/US2021/053162, mailed Mar. 28, 2022, 18 pages.
International Search Report and Written Opinion for the International Patent Application No. PCT/US2021/064041, mailed Apr. 29, 2022, 11 pages.
International Search Report and Written Opinion for the International Patent Application No. PCT/US2022/015809, mailed Jun. 20, 2022, 15 pages.

\* cited by examiner

EXERCISE SAFETY PREDICTION BASED ON PHYSIOLOGICAL CONDITIONS

RELATED APPLICATIONS

This application claims the benefit of U.S. Provisional Patent Application No. 63/197,613, filed Jun. 7, 2021, the contents of which are incorporated herein by reference in their entirety.

BACKGROUND

Maintaining healthy lifestyle is both critically important to patients with Type 1 diabetes and challenging at the same time. Many patients have a challenge to maintain their blood glucose level at an appropriate level during or after exercise and may have to take rescue snacks if there is a concern of hypoglycemia. Exercise increases insulin sensitivity and muscle cells are better able to use any available insulin to take up glucose during and after activity. Moreover, during exercise, muscle cells absorb glucose for energy, whether insulin is available or not. As a result, glucose in the blood decreases, leading to potential hypoglycemic events, and causing diabetics to feel fearful of exercise and hypoglycemia due to the over delivery of insulin during or after exercise.

These situations can become more difficult to manage if the patient has a high amount of insulin onboard (IOB) or just had either a post-prandial bolus or a correction bolus. The excess insulin followed by exercise activity may further increase the risk of hypoglycemia as insulin absorption increases from exercise, the exercise itself causes the body to metabolize glucose more quickly, and the additional insulin further acts to reduce blood glucose.

BRIEF SUMMARY

In one aspect, a wearable drug delivery device includes a processor, a pump mechanism, a memory, and a reservoir. The reservoir may contain a liquid drug. The pump mechanism may be communicatively coupled to the processor and fluidically coupled to the reservoir. The memory may be coupled to the processor and operable to store programming code that, when executed by the processor, causes the processor to be operable to receive data indicating physiological conditions of a wearer of the wearable drug delivery device, and evaluate the obtained data with relation to the wearer participating in exercise. The processor may determine whether it is safe for the wearer to participate in exercise based on a result of the evaluation and output an exercise safety signal indicating a result of the determination of whether it is safe or unsafe for the wearer to participate in exercise.

In another aspect, an automatic, wearable drug delivery system may include a drug delivery device and a controller. The drug delivery device may include logic circuitry operable to control the drug delivery device, a reservoir configured to contain a liquid drug, a communication device coupled to the logic circuitry and a pump mechanism responsive to the logic circuitry and fluidically coupled to the reservoir. The controller may include a processor and a memory. The memory may be coupled to the processor and configured to store a medication delivery application, an exercise safety application, and programming code. When the exercise safety application is executed by the processor, the processor is operable to receive an input from the wearer related to a physiological condition of a wearer. The processor may evaluate data parameters related to physiological conditions of a wearer and the received input related to the physiological condition of a wearer and determine whether the wearer has participated in exercise. The processor, in response to a determination that the wearer has participated in exercise and a result of the evaluation of the data parameters, may generate an exercise safety signal, and present an indication of a result of an interpretation of the exercise safety signal at a user interface. The indication is a safe or unsafe indicator. In response to the generation of the exercise safety signal, the processor may modify a medication treatment plan.

In a further aspect, a non-transitory computer-readable storage medium is provided that may include instructions that, when executed by a processor, cause the processor to determine that a wearer of a wearable drug delivery device is participating in exercise. The instructions may cause the processor to modify an insulin onboard curve in response to the determination that a wearer is participating in exercise and use the modified insulin onboard curve to calculate a next dosage of insulin to be delivered to the wearer and calculate a time to deliver the next dosage. The instructions may trigger the processor to cause the next dosage of insulin to be delivered at the calculated time to the wearer.

DETAILED DESCRIPTION

Systems, devices, computer-readable medium and methods in accordance with the present disclosure are now described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure is thorough and complete, and may fully convey the scope of methods and devices to those skilled in the art. Each of the systems, devices, and methods disclosed herein provides one or more advantages over conventional systems, components, and methods.

Various examples provide a method, a system, a device and a computer-readable medium for responding to inputs provided by sensors, such as an analyte sensor, and wearers (i.e., users) of an automatic drug delivery system. "Analyte sensor" may refer to a wearable device that includes sensing and measurement devices configured to detect different analytes in a wearer's body and particularly in the user's blood, such as blood glucose levels, and/or other analytes as described herein. The various devices and sensors that may be used to implement some specific examples may also be used to implement different therapeutic regimens using different drugs than those described in the specific examples.

The disclosed examples provide techniques related to the safety of a wearer to participate in exercise that may be used with any additional algorithms or computer applications that manage blood glucose levels and insulin therapy. These algorithms and computer applications may be collectively referred to as "medication delivery algorithms" or "medication delivery applications" and may be operable to deliver different categories of drugs (or medications), such as chemotherapy drugs, pain relief drugs, diabetes treatment drugs (e.g., insulin, glucagon and/or glucagon-like peptides), blood pressure medication, or the like.

A type of medication delivery algorithm (MDA) may include an "artificial pancreas" algorithm-based system, or more generally, an artificial pancreas (AP) application. For ease of discussion, the computer programs and computer applications that implement the medication delivery algorithms or applications may be referred to herein as an "AP application." An AP application may be configured to provide automatic delivery of insulin based on an analyte sensor input, such as signals received from an analyte sensor, such as a continuous blood glucose monitor, or the like. The signals from the analyte sensor may be blood glucose measurement values, or the like.

Figure 1:
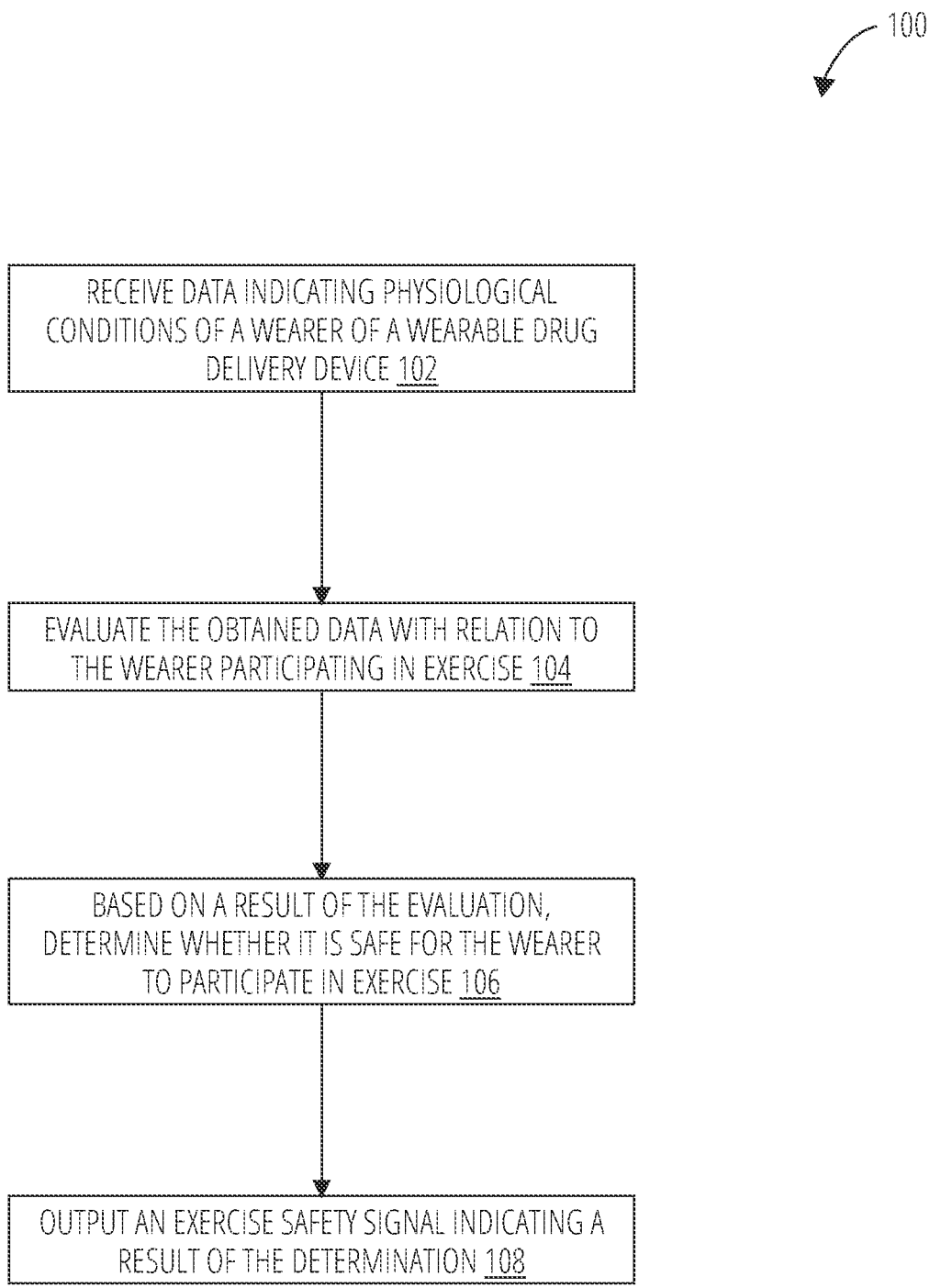
FIG. 1 is a flowchart of an example process implemented according to an aspect of the disclosed subject matter.

In one aspect, a wearable drug delivery device may be operable to determine whether it is safe for a wearer of the drug delivery device to participate in exercise at a present time or future time. The wearable drug delivery device may include, for example, a processor, a reservoir, a pump mechanism, a communication device, and a memory. The reservoir may be configured to contain a liquid drug. The pump mechanism may be communicatively coupled to the processor and fluidically coupled to the reservoir. The memory may be coupled to the processor and configured to store programming code that, when executed by the processor, is operable to perform different functions. The wearable drug delivery device may be communicatively coupled to a controller device. The controller device may have a processor and memory as well as communication devices that enable communication with the wearable drug delivery device and also external devices and systems, such as cloud-based services. FIG. 1 is a flowchart of an example process implemented according to an aspect of the disclosed subject matter.

The process 100 may be executed by the processor of the controller as the controller processor may have greater computational power than a processor of the wearable drug delivery device. In addition, the controller memory may maintain a greater amount of historical data than the memory of the wearable drug delivery device.

In block 102, the processor when executing the programming code that implements process 100 may receive data that indicates physiological conditions of a wearer of the wearable drug delivery device. The received data may include a current blood glucose measurement value or data indicative thereof, a total daily insulin value, an amount of a requested bolus, a time at which the bolus was requested, a current insulin onboard value, or an amount of insulin delivered within a past evaluation period. A past evaluation period may be a previous cycle, such as 5 minutes, or another period of time such as a past 15-minute period, a 30-minute period, a 60-minute period, a 120 minute period of time, or a set time period such as when a wearer may most likely exercise, such as between 5 am and 7 am, 12 pm to 1 pm, or the like.

In addition, or alternatively, the processor, when executing the stored programming code, may be further operable to retrieve physiological data from the memory, where the physiological data may contain a number of days of data related to the wearer's participation in exercise. The processor may use the received data, the retrieved physiological data or both to update an exercise model.

In block 104, the process 100 may evaluate the obtained data with relation to the wearer participating in exercise. For example, the processor, when evaluating the obtained data with relation to the wearer participating in exercise, may be operable to input values obtained from the received data into an exercise model (which may be the updated exercise model), and analyze an output of the exercise model with reference to threshold values related to exercise safety for the wearer. The threshold values related to exercise safety may be parameters that are weighted differently for each wearer according to wearer demographics, disease progression (e.g., type 2 diabetes versus type 1 diabetes), or the like.

In block 106, the processor implementing process 100 may, based on a result of the evaluation, determine whether it is safe for the wearer to participate in exercise. For example, the processor may be further operable to determine whether the result of the evaluation indicates a presence of one or more conditions and based on the determination of the presence of the one or more conditions. For example, the output of the exercise model may indicate whether it is safe or unsafe for the wearer to exercise and the processor may use the output from the exercise model to make the determination.

In addition, or alternatively, the processor, when determining whether it is safe for the wearer to participate in exercise, may be further operable to determine whether the result of the evaluation indicates that a trajectory of blood glucose measurement values of the wearer is trending downward. Based on the determination that the trajectory of the glucose measurement values of the wearer are trending downward, the processor may generate an indication that exercise is unsafe. For example, the downward trend may be a rate of change of (−) 100 mg/dL per hour for the trajectory of blood glucose measurement values of the wearer. A downward trend may also be referred to as a negative rate of change or a negative (or downward) trajectory of blood glucose measurement values. Of course, rates of change other than (−) 100 mg/dL may be used, such as (−) 10 mg/dL, (−) 50 mg/dL, (−) 75 mg/dL, (−) 90 mg/dL, or the like. Additionally, or alternatively, the output of the exercise model may indicate whether it is safe or unsafe for the wearer to exercise based on a current or future predicted value of the user's blood glucose level. For example, the exercise model may make a prediction based on current blood glucose trends where the user's blood glucose measurement value will be in 30 minutes or 1 hour, and if this predicted value is less than X mg/dL (e.g., where X is approximately 70, 80, 90, 100, or 110 mg/dL), the processor may output an indication that it is unsafe to exercise, or an indication that it is unsafe to exercise for the next Y minutes (for example, where Y is approximately 30 or 60 minutes), or an indication that it is unsafe to exercise unless the user consumes food or carbohydrates, or an indication that it is safe to exercise, or a combination of these potential outputs.

In block 108, process 100 may cause output of an exercise safety signal indicating a result of the determination of whether it is safe for the wearer to participate in exercise. Based on the determination of whether it safe or unsafe for the wearer to participate in exercise, the processor may generate an indication that exercise is unsafe. Alternatively, the processor may generate that exercise is safe. For example, as described in more detail with reference to other figures, the wearable drug delivery device may also include an output device coupled to the processor. The processor may be further operable to interpret the outputted exercise safety signal. Based on the interpretation, the processor may provide an output signal to the output device based on the outputted exercise safety signal.

For example, the processor may interpret the outputted exercise safety signal as indicating that it is unsafe for the user to exercise. The processor may output command signals that cause the output device to make outputs that are indications of unsafe exercise situations, such as vibrating in a particular pattern of vibrations (e.g., Morse code for distress—S-O-S), make a sound (e.g., a particular beeping sound or number of beeps), change color (e.g., turn from "green" to "yellow" or "red" depending upon the level of urgency (i.e., the degree of unsafety)), or the like. Alternatively, in response to the processor interpreting the outputted exercise safety signal as indicating it is safe to exercise, the processor may output command signals that cause the output device to make outputs that are indications of safe exercise situations, such as vibrating in a particular pattern of vibrations (e.g., 2 vibrations, or the like), make a sound (e.g., a different beeping sound or number of beeps as compared with an unsafe signal), change color (e.g., turn from no lights to a "green" light or from "yellow" to "green"), or the like. Alternatively, if the processor interprets the exercise safety signal as indicating it is safe to exercise, the processor may not generate any output signals.

In addition, or alternatively, the processor may be further operable to modify a medication treatment plan based on the outputted exercise safety signal. For example, if the processor outputs an exercise safety signal indicating it is unsafe to exercise, but the wearer is determined to participate in exercise, the processor may cause all delivery of insulin to cease for a period of time or reduce an amount of insulin that may be delivered to the user for period of time, included in manual bolus dosages. The cessation or reduction may vary from wearer to wearer.

The determination that the wearer is participating in exercise may be made according to various techniques. For example, the wearer may self-report the participation in exercise by inputting exercise participation in a graphical user interface (provided via an exercise detection application or the AP application) presented on a display of a controller. Alternatively, the controller and/or wearable drug delivery device may have sensors, such as an accelerometer, global positioning system (GPS) signals, Wi-Fi signals, gyroscopes, or the like, that output signals in response to movement by the wearer, a change in location, or an indication of location. Using the information provided by one or more of the respective sensors, the processor when evaluating the information may determine that the information has previously indicated participation in exercise or a location where exercise takes place (e.g., a gym, a ballpark, soccer field, or the like). In addition, or alternatively, the processor may execute an exercise detection application or algorithm that is operable to evaluate inputs from the sensors as well as location information based on the GPS or Wi-Fi signals, information obtained from other mobile computer applications, such as fitness applications, calendar applications (e.g., fitness class schedules, athletic team schedules, or the like). Based on the evaluated inputs, such as high acceleration values for an extended period of time (duration threshold) or a certain number of high acceleration values within another set threshold period of time, a calendar entry indicating the current time as a scheduled time of a fitness class, the processor may determine above a preset probability that the wearer is participating in exercise.

Other technical features may be readily apparent to one skilled in the art from the following figures, descriptions, and claims.

Figure 2:
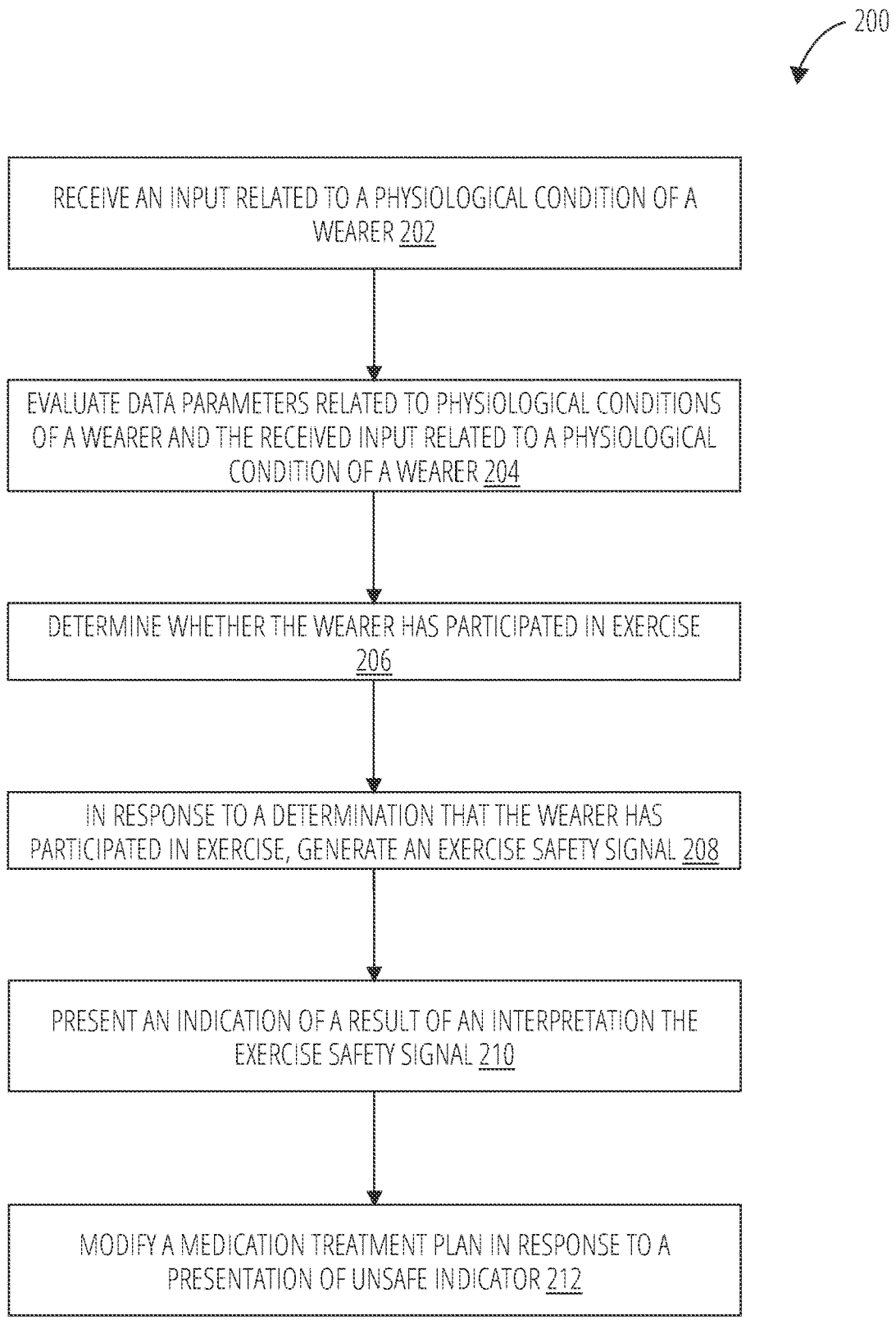
FIG. 2 is a flowchart of another example process implemented according to a further aspect of the disclosed subject matter.

In another aspect, a wearable drug delivery system may include a drug delivery device, an analyte sensor, and a controller as well as other devices described with reference to other examples. FIG. 2 is a flowchart of another example process implemented according to a further aspect of the disclosed subject matter. The process 200 may be executed by a processor such as the processor of a controller (shown in other examples). For example, the controller may be a smartphone or a dedicated mobile computing device. The processor of the controller may be operable to execute many computer applications including a calendar application, a fitness application, a medication delivery application that utilizes an exercise safety algorithm, such as process 200, and the like.

In block 202, the processor may receive an input related to a physiological condition of a wearer. The input may, for example, be from the wearer or from an exercise safety algorithm. In an example, the wearer may request a bolus, use a hypoglycemia protect mode, or indicate that they are about to participate in exercise, or schedule a time at which they will participate in exercise.

In block 204, in response to the received input related to a physiological condition of a wearer, the process 200 may evaluate data parameters related to one or more physiological conditions of a wearer. The data parameters related to physiological conditions of a wearer may, for example, include a blood glucose measurement value, a total daily insulin amount, a current calculation of an amount of insulin onboard, and an amount of insulin delivered in a past evaluation period.

For example, the processor, when evaluating the data parameters, may be further operable to input data parameters including a blood glucose measurement value, a total daily insulin value, a time and an amount of a requested bolus, an amount of insulin onboard value, or an amount of insulin delivered within a past evaluation period, into an exercise model. The result of the evaluation of the data parameters at block 204 may be an indication that exercise is unsafe or safe at the time of the evaluation. For example, the data parameters may be evaluated utilizing a machine-learning, exercise model that outputs a value indicating whether participation in exercise by a user or wearer is safe or unsafe.

In block 206, the processor determines whether the wearer has participated in exercise. Participation in exercise may be determined as mentioned above with reference to the exercise determination in FIG. 1. In addition, or alternatively, the determination of exercise participation may be made based on an analysis of different attributes and factors, such as the user's calendar application on the controller, an exercise input entered through a user interface of the controller, an exercise detection application executing on the controller, based on outputs from other sensors on the controller, such as an accelerometer, gyroscope, camera or microphone, or the like. The factors or attributes may be inputs into an exercise model that is operable to determine whether exercise is safe or unsafe based on physiological conditions of a wearer.

In block 208, in response to a determination that the wearer has participated, or is participating, or will participate in exercise, the processor may generate an exercise safety signal. For example, the processor may use the result of the evaluation of the data parameters obtained in block 204 when generating the exercise safety signal. For example, after participating in exercise, the wearer may indicate that they are feeling "dizzy" or "lightheaded," and, as a result, the processor can identify (e.g., label) physiological data (e.g., data parameters such as blood glucose measurement values, a total daily insulin amount, a current calculation of an amount of insulin onboard, and an amount of insulin delivered in a past evaluation period) that correspond to the indicated feeling of dizziness or lightheadedness.

Additionally, the processor may be operable to control a communication device to establish a wireless communication connection with an external device, where the external device is a data network device (shown in another example) or a cloud-based service (also shown in another example) to access external devices or services, and retrieve physiological data from a memory source (such as cloud-based storage or the like), where the physiological data contains a number of days of data related to the wearer's participation in exercise. The wearable drug delivery device may also include updates to an exercise model using the retrieved physiological data.

In block 210, process 200 when executed may cause the processor to present an indication of a result of an interpretation of the exercise safety signal, wherein the indication is a safe or unsafe indicator for exercise participation. For example, the presentation of the safe or unsafe indicator may be on a display of a controller, such as a touchscreen display, or a user interface of a drug delivery device, or the like.

Alternatively, in a further embodiment, based upon the construction of the exercise model, personalized data and daily blood glucose measurement value trend averages, the processor may suggest the best suitable times for the wearer to participate in exercise. As such, the presented indication may suggest to the wearer to wait 15 minutes, 30 minutes or the like before participating, suggest alternative exercises to perform (e.g., weightlifting (short bursts) versus a long run (an extended high heart rate), or recommend ingesting carbohydrates (e.g., consuming a snack or the like) before exercising.

In addition to predicting safe or unsafe conditions, the exercise model may be further trained to predict a class of probabilities that may be used as threshold values related to exercise safety. In this case, the model may predict which intensity of the exercise may be unsafe. For example, for given physiological conditions of a wearer, high intensity training may not be suitable at this time for the wearer, but a brisk walk or yoga might be acceptable. The recommendations for the type of exercise to participate in and/or to avoid may be presented to the wearer via a user interface of a controller or other device. In addition, or alternatively, a class of probabilities may be selected such that the model favors false positives over false negatives because the consequences of false negatives are higher. This is similar to screening tests where further investigation is needed. In this example, the model may favor a conservative approach where a signal indicating that it is unsafe to exercise is better than the converse. The probabilities could be constructed by retrospect of past glucose distributions under the same activities. For example, if a current blood glucose measurement value is below the 10th percentile of the blood glucose measurement values during past training activities, then the processor executing an exercise safety algorithm may determine that it is not safe for the wearer to do the same activity as in the past training activities at this time.

In block 212, the processor when executing process 200 may cause a medication delivery application to modify a medication treatment plan in response to a presentation of unsafe indicator. For example, if the processor determines it is unsafe to exercise the processor may withhold delivery of insulin for a period of time. Alternatively, if the processor determines it is safe to proceed with exercise, the processor may cause a modification of a dosage of insulin but continue with the presently set delivery schedule for the next dose.

Either of the steps in block 210 or 212 may be optional depending upon user preference settings or clinician settings or other settings (e.g., default settings). For example, a user preference may be set to notify the user only when exercise is unsafe and no notification when exercise is safe. Other user preference settings may be, for example, to receive notifications whether exercise is safe or unsafe, or receive a notification only when exercise is determined to be safe. It may be helpful to have a couple of exemplary physiological conditions of a wearer as well as other factors that are evaluated by the exercise model.

Each row of Table 1 below may represent a different day for a particular wearer or a group of different wearers. In the table below, the exercise model may evaluate the physiological data related to the physiological conditions of a wearer, such as one or more blood glucose measurement values provided by a continuous glucose monitor (CGM), an indication of whether any blood glucose measurement values were missed, a number of boluses delivered, an amount of insulin (in Units) delivered within the last 30 minutes, whether the wearer's blood glucose measurement value was within the hypoglycemic range (for the wearer, such as, for example, 60 mg/dL or lower), a calculated amount of insulin onboard (IOB) for the wearer, the wearer's target blood glucose setting, and the wearer's TDI. The label is the binary indication of safe to exercise (Label=0) or unsafe to exercise (Label=1).

TABLE 1

| CGM | Missed count | bolus | Insulin in last 30 min | intensity of exercise | IOB | setpoint | TDI | label |
|---|---|---|---|---|---|---|---|---|
| 160 | 0 | 0 | 0 | 1 | 0.421 | 110 | 45 | 0 |
| 159 | 0 | 0 | 4 | 1 | 0.374 | 110 | 100 | 0 |
| 158 | 1 | 0 | 10 | 2 | 4.332 | 110 | 21 | 1 |
| 153 | 0 | 2 | 0 | 1 | 0.257 | 110 | 25 | 0 |
| 152 | 1 | 0 | 0 | 1 | 0.225 | 110 | 32 | 0 |
| 151 | 1 | 0 | 4 | 1 | 0.196 | 110 | 5 | 0 |
| 206 | 5 | 0 | 5 | 1 | 0.456 | 110 | 40 | 0 |
| 200 | 0 | 0 | 6 | 2 | 1.444 | 110 | 10 | 1 |
| 192 | 0 | 0 | 0 | 0 | 0.430 | 110 | 30 | 0 |

TABLE 1-continued

| CGM | Missed count | bolus | Insulin in last 30 min | intensity of exercise | IOB | setpoint | TDI | label |
|---|---|---|---|---|---|---|---|---|
| 149 | 0 | 0 | 0 | 0 | 0.321 | 110 | 65 | 0 |
| 80 | 0 | 5 | 3 | 0 | 1.301 | 110 | 40 | 1 |
| 132 | 0 | 0 | 0 | 0 | 0.280 | 110 | 21 | 0 |
| 126 | 0 | 0 | 0 | 0 | 0.260 | 110 | 21 | 0 |
| 72 | 0 | 2 | 10 | 0 | 3.073 | 110 | 50 | 1 |
| 71 | 0 | 0 | 2 | 0 | 0.064 | 110 | 21 | 0 |
| −1 | 18 | 4 | 5 | 2 | 1.031 | 110 | 90 | 1 |
| 70 | 1 | 0 | 2 | 0 | 0.026 | 110 | 100 | 0 |

The "intensity of the exercise" data point indicates how intense the exercise is to the user, for example, intensity values may be: 1=normal (E.g. normal walk, etc.), 2=moderate (brisk walk, biking, etc.), and 3=intense (high intensity interval training (HIIT), running, etc.)

In an example using the third row of Table 1 above, the exercise model may indicate that the physiological data in the third row triggers an unsafe exercise response as indicated by the label=1. The basis for the exercise model indicating that the physiological data indicates may be based for example on a low TDI of 21 Units (U), the 10 U insulin in past 30 minutes, and a current IOB of approximately 4.332 Units. Together, these parameters, when combined with the user's performance of intense exercise, or perhaps even mild exercise (given the particular user of a wearable drug delivery device), and when evaluated by the exercise model, may indicate that participation in exercise by the user is either safe or unsafe.

The other rows of data that resulted in being labeled unsafe were based on various factors. For example, the row in which the CGM value is 200, the data that generated the unsafe to exercise indication was based on the low TDI (10), the 6 U of insulin in the past 30 mins, current IOB of approximately 1.444 U. Similarly, the third indication of unsafe to participate in exercise is in the CGM reading of 80, the data that generated the unsafe to exercise indication was based on a low CGM reading (80), a medium range TDI of approximately 40, the medium range IOB of approximately 1.301, and the 5 U requested bolus. The fourth indication of unsafe to participate in exercise is in the CGM reading of 72, the data that generated the unsafe to exercise indication was based on a low CGM reading (72), a medium range TDI of approximately 50, the higher IOB of approximately 3.703, the 10 U of insulin in the last 30 minutes, and the 2 U requested bolus. The fifth indication of unsafe to participate in exercise is in the CGM reading of −1, which suggests that CGM readings have been missed past a threshold amount (for example, for the past 30 minutes), and in this case, for past 90 minutes (5 minutes times 18 missed readings), the medium range of IOB of approximately 1.031, the 5 U of insulin in past 30 mins, a requested bolus of 4 U and the TDI of 90.

Based on the label, the programming code may cause the processor to generate an exercise safety signal indicating whether exercise is safe or unsafe. The processor may respond to the generated exercise safety signal as discussed above. The exercise model may be a machine learning model, such as a linear regression model, a logistic regression model, a decision tree model, a support vector machine, a naïve Bayes classifier, or the like.

It may be helpful to describe at a high level, details related to the exercise model, which in the example below is a logistic regression model, and, in particular, how the exercise model may be built, trained, and modified, if necessary.

The exercise model may be generated by a processor in a server, such as a cloud-based server, or the like.

In an operational example of how the logistic regression exercise model is built; a processor may be further configured to obtain data from a dataset including physiological data indicating physiological conditions of the wearer. The processor may split data in the dataset into training data and validation data. Using the training data, a logistic regression model may be trained. The validation data may be used to validate an output of the logistic regression model. Based on a result of the validation of the output of the logistic regression model, the processor may perform hyperparameter tuning to improve the accuracy of the logistic regression model. The processor may retrieve the received data related to physiological conditions of the wearer and input the retrieved current data into the logistic regression model for evaluation. The processor may, for example, label the output data as either indicating an unsafe condition for exercise or a safe condition for exercise based on a value of output data from the logistic regression model. The processor may generate an exercise safety signal based on any label indicating an unsafe condition for exercise.

Once you build a classifier and enable a Boolean output, the classifier may provide a probability related to whether it is safe to exercise. A threshold based on past history (whether it was safe to exercise in the past) may be established, and everything above threshold would be true, everything below would be false. Boolean value of true or 1 would be unsafe to exercise.

Other technical features may be readily apparent to one skilled in the art from the following figures, descriptions, and claims.

Figure 3:
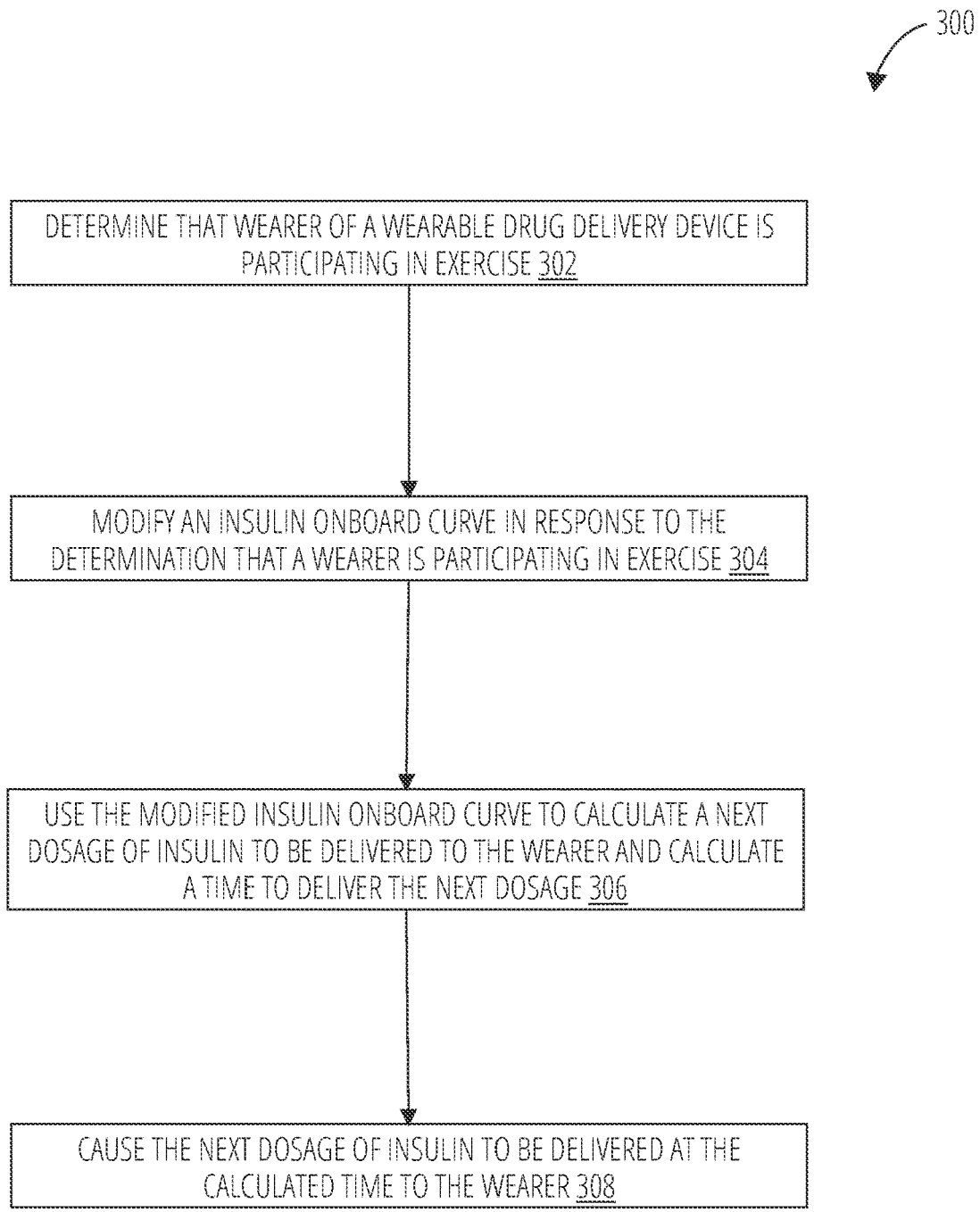
FIG. 3 is a flowchart of a further example process implemented according to another aspect of the disclosed subject matter.

FIG. 3 is a flowchart of a further example process implemented according to another aspect of the disclosed subject matter.

A processor or logic circuitry may be operable to execute programming code stored in a memory coupled to the respective processor or logic circuitry. In block 302, a processor executing process 300 may be operable to determine that a wearer of a wearable drug delivery device is participating in exercise. It is noted that exercise can have both short- and long-term physiological effects.

Once participation in exercise is detected, the system can implement a long-term lengthening of the IOB curves over a period of 12-24 hours following exercise to account for the long-term effects of exercise. For example, as shown in block 304, the process 300 modifies an insulin onboard curve in response to the determination that a wearer is participating in exercise. The processor when executing process 300 may modify the insulin onboard (JOB) curve by extending a length of the insulin onboard curve. Extending the length of the IOB curve slows decay of a calculated amount of insulin onboard and the extension remains in place for a preset period of time.

The modification of the IOB curve makes the processor evaluate the effect of exercise based on changing the effective IOB (i.e., the amount of insulin onboard that will be metabolized by the wearer's body over time), while the wearer's sensitivity to insulin remains unchanged because a change to sensitivity would be a direct change to the exercise model. Instead, the modification of the length of the IOB curve makes a change to the perceived length of time the insulin is acting in the wearer's body. Based on the extended IOB curve, the processor may modify constraints that are applied to the insulin doses (e.g., limits on the maximum amount of insulin that is included in a bolus, delivered within X number of hours of the determined participation in exercise, or the like, where X is approximately 3.5 to approximately 4.5) but the medication delivery algorithm continues making insulin delivery decisions based on threshold values related to exercise safety and the modified constraints. For instance, the assumed 3-hour and 4-hour IOB decay curves may be lengthened to 3.5 hours and 4.5 hours following detection of significant exercise, to incorporate the impact of relatively longer-lasting increased insulin sensitivity. Of course, other values of X may be 1.5, 2, 6, 12 or the like. This is illustrated in the example IOB curves of FIG. 5.

In block 306, the processor implementing process 300 may use the modified insulin onboard curve to calculate a next dosage of insulin to be delivered to the wearer and calculate a time to deliver the next dosage.

In block 308, the process 300 may cause the next dosage of insulin to be delivered at the calculated time to the wearer.

Other technical features may be readily apparent to one skilled in the art from the following figures, descriptions, and claims.

Figure 4:
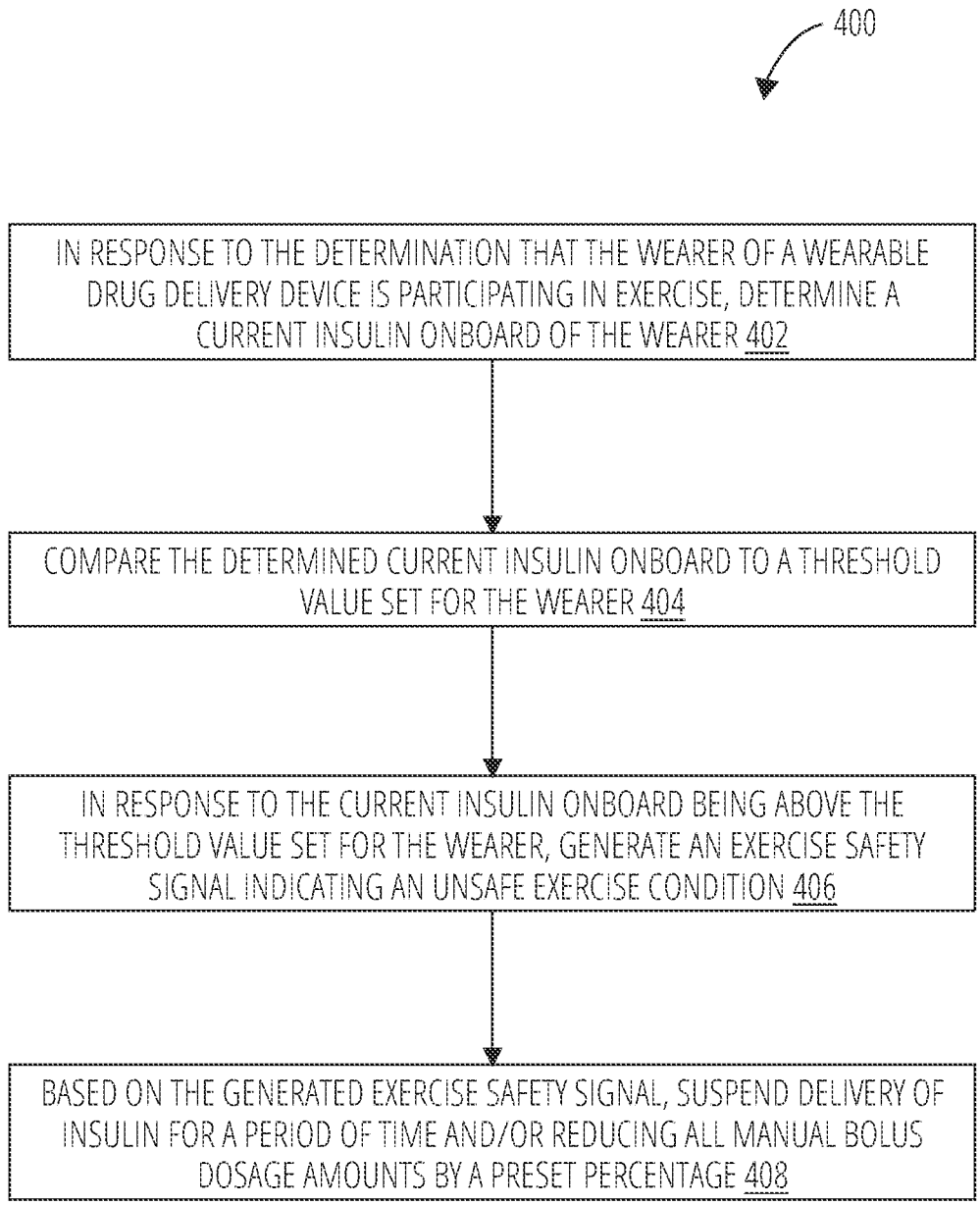
FIG. 4 illustrates in a flowchart a process in accordance with an embodiment of the disclosed subject matter.

FIG. 4 illustrates a process 400 in accordance with an embodiment of the disclosed subject matter.

In block 402, a processor executing process 400 may be operable to, in response to the determination that the wearer of a wearable drug delivery device is participating in exercise, determine a current insulin onboard of the wearer.

In block 404, process 400 compares the determined current insulin onboard (IOB) to a threshold value set for the wearer. The threshold value for insulin onboard may be one of the threshold values related to exercise safety that is evaluated by the processor. In this example, the current IOB may be a primary factor used in the determination of whether participation in exercise is safe or unsafe for the wearer of the wearable drug delivery device. For example, an IOB of 3 U or greater may indicate that the artificial pancreas application is overcompensating or overdelivering insulin, and hence it is unsafe for the user to exercise. Further, the processor may also determine whether the wearer's total daily insulin (TDI) is going to reach a threshold TDI value, such as, for example, 4 times, 5 times, or 9 times the expected total daily insulin delivery in a 3-hour period of time or another period of time, such as 2-hour period of time, and hence make a determination that it is unsafe to exercise. Alternatively, another threshold may be one in which the total insulin delivered over the last 3 hours, including manual boluses and system automated deliveries, in not permitted to exceed 15 times the number of basal hours, or 31% of TDI. Of course, other TDI thresholds that indicate overcompensation or over delivery may be used.

In block 406, process 400 in response to the current insulin onboard being above the threshold value set for the wearer, generates an exercise safety signal indicating an unsafe exercise condition. In block 408, process 400 based on the generated exercise safety signal, suspends delivery of insulin for a period of time and/or reducing all manual bolus dosage amounts by a preset percentage, such as 25%, 50%, 75%, or in some cases 100%.

Figure 5:
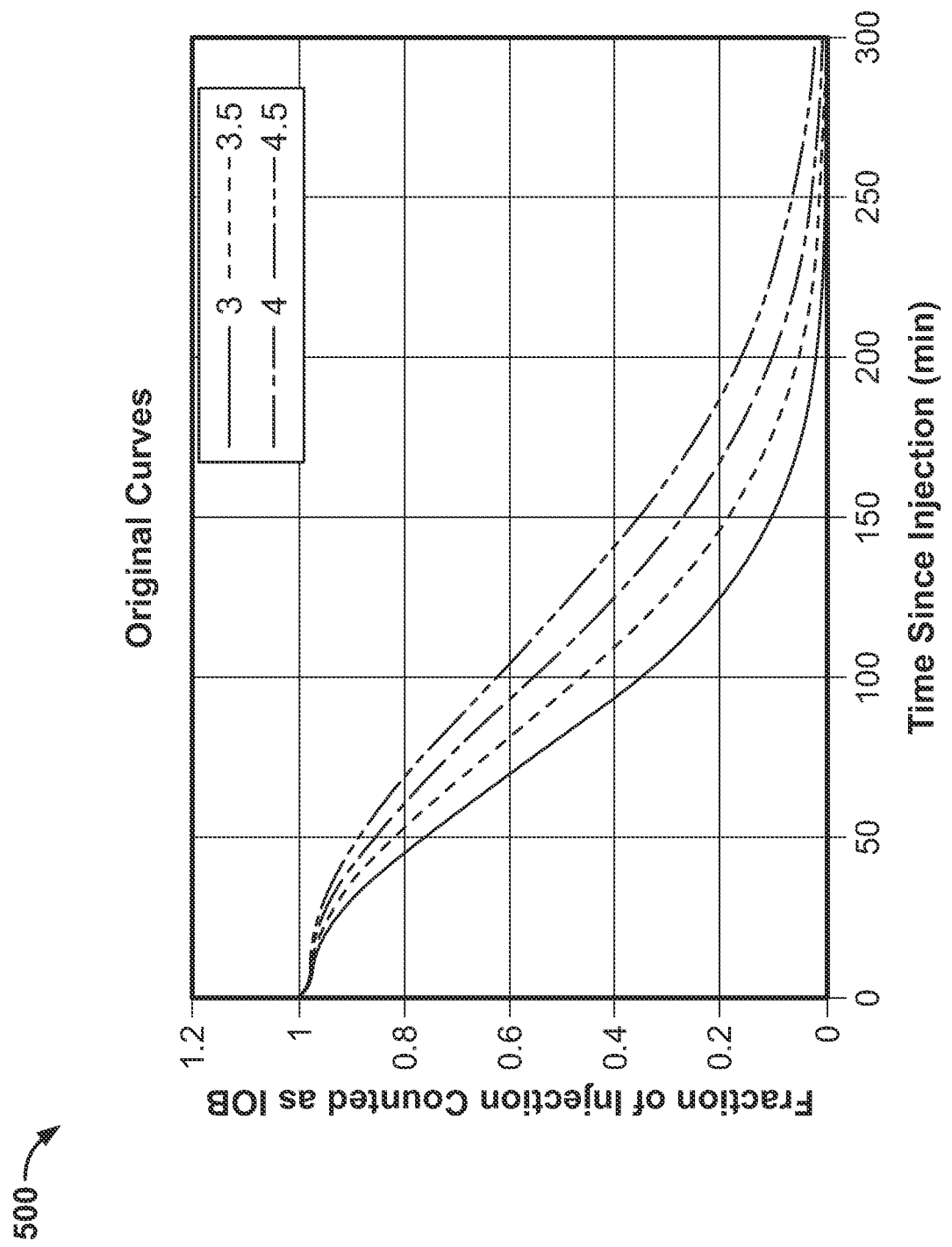
FIG. 5 is a modified insulin onboard decay curve that illustrates an example usable in an embodiment of the disclosed subject matter.

FIG. 5 is a modified insulin onboard decay curve that illustrates an example usable in an embodiment of the disclosed subject matter.

In modified insulin onboard decay curve 500 of FIG. 5, the solid line represents the original 3-hour curve, the dashed line represents the 3-hour insulin decay curve that has been extended by 30 minutes (i.e., the 3.5-hour insulin delay curve), the 4-hour insulin delay curve is shown as dash-dot-dash, and the dashed-dot-dot-dashed line represents the respective 4-hour insulin decay curve extended by 30 minutes (i.e., the 4.5-hour insulin delay curve). As can be seen in the curves, for example, at the $100^{th}$ minute mark, the remaining insulin action is approximately 36% with the 3-hour insulin delay curve, but approximately 46% with the 3.5-hour insulin delay curve, resulting in increased estimated remaining insulin on board and thus potentially a more conservative insulin delivery by the algorithm. If IOB is higher, the insulin delivery algorithm will tend to deliver less insulin.

The modifications of the IOB curves may vary based on the system's original IOB curves that are utilized. The original IOB curves may be based on anonymized, clinical data gathered from hundreds or thousands of patients or based on a specific wearer's history.

Figure 6:
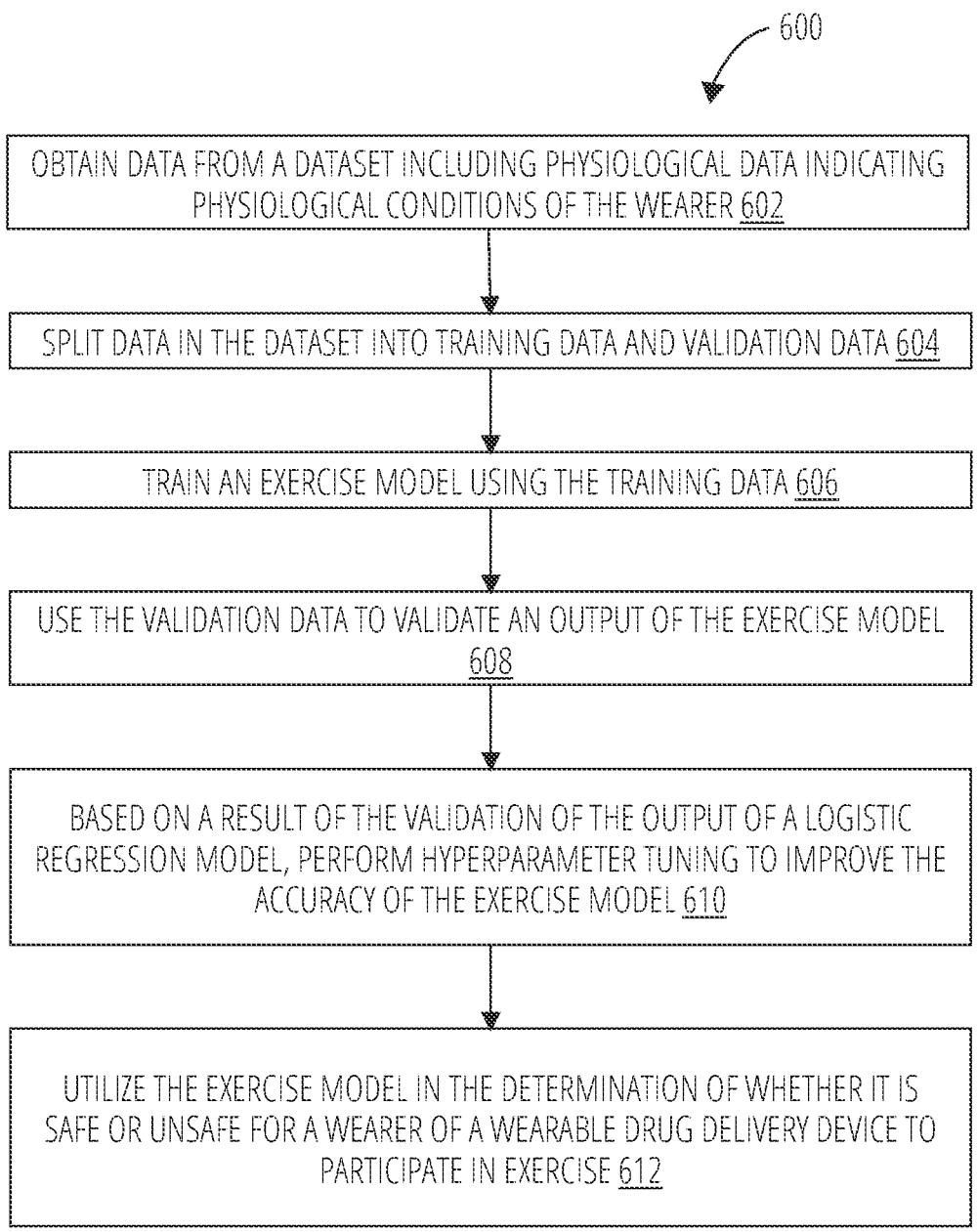
FIG. 6 illustrates an example of a process for generating an exercise model usable with the aspects of the disclosed subject matter.

FIG. 6 illustrates an example of a process for generating an exercise model usable with the aspects of the disclosed subject matter. The generation of the exercise model may occur in a server, such as a server provided by cloud-based services or the like, that is also communicatively coupled to the controller as described with reference to a later example.

As previously mentioned, the exercise model may be a machine learning model that is capable of modifying its output based on the values input into the model and a closeness of the output value to a result produced from a validation data set. In the following discussion of routine 600, the exercise model is implemented as a logistic regression model.

In block 602, a server executing routine 600 may obtain data from a dataset that includes physiological data indicating physiological conditions of the wearer. For example, the controller may be operable to upload anonymized physiological data indicating the physiological conditions of the wearer to the cloud-based services. The data uploaded from the controller may be combined with similar anonymized data that is uploaded from other controllers. Alternatively, the controller may be operable to obtain and process the data. For example, the controller may obtain the data from a memory coupled to the controller or from a server or data storage accessible through cloud-based services. The obtained data may be an entire data set or part of a data set, such as a past evaluation period which may be three, six, nine days, or the like.

In block 604, the server or the controller may split data in the dataset into training data and validation data.

In block 606, a logistic regression model may be trained by the server or the controller using the training data.

In block 608, the server or the controller may use the validation data to validate an output of the logistic regression model.

Based on a result of the validation of the output of the logistic regression model, the controller or server may in block 610 perform hyperparameter tuning to improve the accuracy of the logistic regression model. Once the exercise model is appropriately trained, the controller may begin executing the exercise model to determine whether it is safe or unsafe for the wearer to participate in exercise based on the wearer's physiological conditions.

For example, the controller may in block 612 be operable to utilize the exercise model in the determination of whether it is safe or unsafe for a wearer of a wearable drug delivery device to participate in exercise.

In the examples described with reference to FIGS. 1-6, a controller may input data related to the physiological conditions of the wearer into the exercise model and obtain an exercise safety signal. The data related to the physiological condition of the wearer may be blood glucose measurement values, IOB, total daily insulin (TDI), and similar data as described above with reference to other examples.

Figure 7:
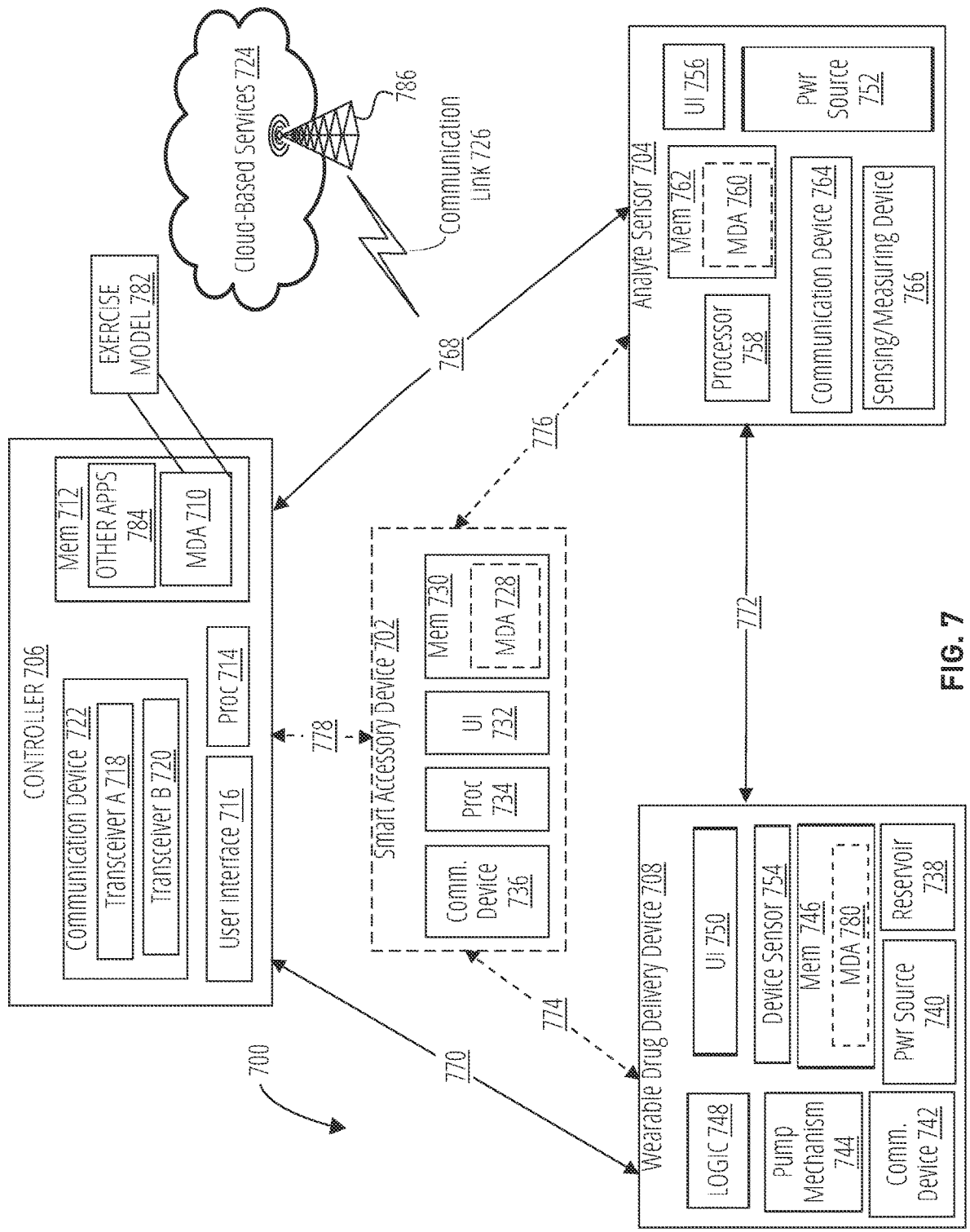
FIG. 7 illustrates a functional block diagram of a system example suitable for implementing the example processes and techniques described herein.

FIG. 7 illustrates a functional block diagram of a system example suitable for implementing the example processes and techniques described herein.

The automatic wearable drug delivery system 700 may implement (and/or provide functionality for) a medication delivery algorithm (MDA), such as an artificial pancreas (AP) application, to govern or control automated delivery of a drug, a therapeutic, or a medication, such as insulin, to a user (e.g., to maintain euglycemia—a normal level of glucose in the blood). The automatic wearable drug delivery system 700 may, for example, include an analyte sensor 704, a controller 706, a wearable drug delivery device 708, and an optional smart accessory device 702.

The controller 706 may be remote from the wearable drug delivery device 708 and may include a user interface 716, a communication device 722, a memory 712, and a processor 714. The user interface 716 is coupled to the processor 714 and operable to receive inputs related to a physiological condition of a wearer and provide the input to the processor 714. In an example, the input may be a request for a bolus dosage. The controller 706 may include a user interface 716, which may be a keypad, a touchscreen display, levers, light-emitting diodes, buttons on the controller 706, a microphone, a camera, a speaker, a display, or the like, that is configured to allow a user to enter information and allow the controller 706 to output information for presentation to the user (e.g., alarm signals, exercise recommendations (e.g., exercise times and/or exercise intensity, and the like). The user interface 716 may provide inputs, such as a voice input, a gesture (e.g., hand or facial) input to a camera, swipes to a touchscreen, or the like, to processor 714 which the programming code interprets.

The controller 706 may be a computing device such as a smart phone, a tablet, a personal diabetes controller, a dedicated diabetes therapy controller, or the like. In an example, the controller 706 may include a processor 714, a controller memory 712, a user interface 716, and a communication device 722. The controller 706 may contain analog and/or digital circuitry that may be implemented as a processor 714 for executing processes based on programming code stored in the controller memory 712, such as the medication delivery algorithm or application (MDA) 710 and/or the exercise model 782 and related programming code as well as threshold values related to exercise safety. In addition, the memory 712 may store programming code to manage a user's blood glucose levels and for controlling the delivery of the drug, medication, or therapeutic agent to the user as well as programming code that determines via the exercise model 782 whether it is safe or unsafe for a wearer (or user) to participate in exercise and cause the execution of different actions in response to the determination, as discussed above. The controller 706 may be used to program, adjust settings, and/or control operation of the wearable drug delivery device 708 and/or the analyte sensor 704 as well as the optional smart accessory device 702.

The one or more transceivers, transceiver A 718 and transceiver B 720 may operate according to one or more radio-frequency protocols. In the example, the transceivers 718 and 720 may be a cellular transceiver and a Bluetooth® transceiver, respectively. For example, the transceiver A 718 or transceiver B 720 may be configured to receive and transmit signals containing information usable in the exercise model 782 by the MDA 710, such as physiological conditions of a wearer, other physiological data, IOB curves and the like.

The wearable drug delivery device 708 may include logic circuitry 748, a reservoir 738, a communication device 742, a power source 740, a memory 712, user interface (UI) 750, and a pump mechanism 744. The logic circuitry 748 may be operable to control the drug delivery device. The reservoir 738 may be configured to contain a liquid drug. The communication device 742 may be coupled to the logic circuitry 748. The pump mechanism 744 may be responsive to the logic circuitry 748 and fluidically coupled to the reservoir 738.

The memory 712 may store programming code executable by the processor 714. The programming code, for example, may enable the processor 714 to control expelling insulin from the reservoir 738 in response to control signals from the controller 706 and MDA 710 or based on signals from the optional MDA 780.

In the example, the communication device 742, which may be a receiver, a transmitter, or a transceiver that operates according to one or more radio-frequency protocols, such as Bluetooth, Wi-Fi, a near-field communication standard, a cellular standard, or the like. The communication device 764 may enable the logic circuitry 748 to communicate with the controller 706 and the analyte sensor 704.

The wearable drug delivery device 708 may be attached to the body of a user, such as a patient or diabetic, at an attachment location and may deliver any therapeutic substance to a user at or around the attachment location. For example, a bottom surface of the wearable drug delivery device 708 may include an adhesive to facilitate attachment to the skin of a wearer.

The reservoir 738 may store drugs, medications or therapeutic agents suitable for automated delivery, such as diabetes treatment drugs (e.g., insulin, glucagon, glucagon-like peptides), pain relief drugs (e.g., morphine), hormones, blood pressure medicines, chemotherapy drugs, or the like. The wearable drug delivery device 708 may include a needle or cannula (not shown in this example) coupled to the reservoir 738 and extending into the body of the wearer for delivering the drug into the wearer's body of the user (which may be done subcutaneously, intraperitoneally, or intravenously), and a pump mechanism 744 under control of the logic circuitry 748 transfers the drug from the reservoir 738 through the needle or cannula and into the wearer.

The power source 740, such as a battery, a piezoelectric device, other forms of energy harvesting devices, or the like, for supplying electrical power to the pump mechanism 744 and/or other components of the wearable drug delivery device 708.

In some examples, the wearable drug delivery device 708 may include a user interface 750, which may be a keypad, a touchscreen display, levers, light-emitting diodes, buttons on a housing of the drug delivery device 708, a microphone, a camera, a speaker, a display, or the like, that is configured to allow a user to enter information and allow the drug delivery device 708 to output information for presentation to the user (e.g., audio, visual or vibrational alarm signals or the like). The user interface 750 may provide inputs, such as a voice input, a gesture (e.g., hand or facial) input to an optical sensor, swipes to a touchscreen, or the like, to processor 714 which the programming code interprets.

The wearable drug delivery device 708 may optionally include a device sensor 754 that may include an accelerometer, a gyroscope, a skin conductance measuring device (e.g., to measure perspiration due to exercise), or the like. Signals from the device sensor 754 may be provided to the controller 706 for use in determining whether a wearer is participating in exercise.

The smart accessory device 702 may be a smart watch, another wearable smart device, including eyeglasses, provided by other manufacturers, a global positioning system-enabled wearable device, a wearable fitness device, smart clothing, or the like, and may be operable to communicate with the other components of system 700 via wireless communication links 774, 776, or 778.

For example, the smart accessory device 702 may include a communication device 736, a processor 734, a user interface 732 and a memory 730. The user interface 732 may be a graphical user interface presented on a touchscreen display of the smart accessory device 702. The memory 730 may store programming code to operate different functions of the smart accessory device 702 as well as an instance of the MDA 728. The processor 734 that may execute programming code, such as MDA 728 for controlling the wearable drug delivery device 708 to implement the processes and techniques of FIGS. 1-6 described herein.

The analyte sensor 704 may include a processor 758, a memory 762, a sensing/measuring device 766, a user interface 756, a power source 752, and a communication device 766. The analyte sensor 704 may, for example, be a blood glucose monitor removably attachable via adhesive, for example, to a body of the wearer. In such an example, the analyte sensor 704 is operable to measure a blood glucose measurement value of the wearer (not shown) and communicate with the controller 706 and the drug delivery device 708 via the communication device 764 under the control of the processor 758. The memory 730 may be configured to store information and programming code, such as an instance of the MDA 760.

The analyte sensor 704 may be configured to detect one or more different analytes, such as lactate, ketones, uric acid, sodium, potassium, alcohol levels, blood glucose, proteins, hormones, or the like, and output results of the detections, such as measurement values or the like, for receipt by one or more of 702, 706 or 708. The analyte sensor 704 may, in an example, be configured to measure the blood glucose value at a predetermined time interval, such as every 5 minutes, or the like. The communication device 764 of analyte sensor 704 may have circuitry that operates as a transceiver for communicating the measured blood glucose values to the controller 706 over a wireless link 768 or with the wearable drug delivery device 708 over the wireless communication link 772. While called an analyte sensor 704, the sensing/measuring device 533 of the analyte sensor 704 may include one or more additional sensing elements, such as a heart rate monitor, a pressure sensor, or the like.

The processor 758 of the analyte sensor 704 may be operable to perform many functions. For example, the programming code stored in the memory 762 may enable the processor 758 to manage the collection and analysis of data detected by the sensing and measuring device 766, such as blood glucose measurement values, providing trend information and the like. The processor 758 may include discrete, specialized logic and/or components, an application-specific integrated circuit, a microcontroller or processor that executes software instructions, firmware, programming instructions stored in memory (such as memory 762), or any combination thereof.

Services provided by cloud-based services 724 may include data storage that stores anonymized data, such as blood glucose measurement values, historical IOB or TDI, maximum and minimum boundary values, therapeutic exogenous substance concentration values, substance sensitivity values, and other forms of data. In addition, the cloud-based services 724 may process the anonymized data from multiple users to provide generalized information related to TDI, insulin sensitivity, JOB, and the like. The cloud-based services 724 may be accessed via data network device 786, which may be a Wi-Fi device, a cellular communication tower, a local area network, a campus wide network or the like.

The wireless communication links 726, 768, 770, 772, 774, and 776 may be any type of wireless link operating using known wireless communication standards or proprietary standards. As an example, the wireless communication links communication links 726, 768, 770, 772, 774, and 776 may provide communication links based on Bluetooth®, Zigbee®, Wi-Fi, a near-field communication standard, a cellular standard, or any other wireless protocol via the respective communication devices communication links 726, 768, 770, 772, 774, and 776.

Software related implementations of the techniques described herein, such as the processes examples described with reference to FIGS. 1-6 may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed AP application and algorithms may be operable to perform various functions related to open loop operations, such as the generation of prompts requesting the input of information such as weight or age. Similarly, a dosage amount of insulin may be received by the AP application or algorithm from a user via a user interface. Other open-loop actions may also be implemented by adjusting user settings or the like in an AP application or algorithm.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible considering this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A wearable drug delivery device, comprising:
   a processor,
   a reservoir configured to contain insulin;
   a pump mechanism communicatively coupled to the processor and fluidically coupled to the reservoir; and
   a memory coupled to the processor and operable to store programming code that, when executed by the processor, causes the processor to:
      use an insulin on board (IOB) curve in determining a basal dose of insulin to deliver to a wearer;
      receive data indicative of a physiological condition of the wearer of the wearable drug delivery device;
      evaluate the received data with relation to the wearer participating in exercise;
      based on a result of the evaluation,
         determine whether it is safe for the wearer to participate in exercise; and
         output an exercise safety signal indicating a result of the determination of whether it is safe or unsafe for the wearer to participate in exercise; and
      where the evaluation determines that the wearer is exercising,
         lengthening the IOB curve, and
         using the lengthened IOB curve to determine a next basal dose of insulin for the wearer.

2. The wearable drug delivery device of claim 1, wherein the processor, when determining whether it is safe for the wearer to participate in exercise, is further operable to:
   determine whether the result of the evaluation indicates a presence of one or more conditions; and
   based on the determination of the presence of the one or more conditions, generate an indication that exercise is unsafe.

3. The wearable drug delivery device of claim 2, wherein the one or more conditions include a blood glucose measurement value, a total daily insulin amount, a request for a bolus or a request to use a hypoglycemia protect mode, a current calculation of an amount of insulin onboard, or an amount of insulin delivered in a past evaluation period.

4. The wearable drug delivery device of claim 1, wherein the processor, when determining whether it is safe for the wearer to participate in exercise, is further operable to:
   determine whether the result of the evaluation indicates that a trajectory of blood glucose measurement values of the wearer is trending downward; and
   based on the determination that the trajectory of the glucose measurement values of the wearer are trending downward, generate an indication that exercise is unsafe.

5. The wearable drug delivery device of claim 1, wherein the processor, when executing the stored programming code, is further operable to:
retrieve physiological data from the memory, wherein the physiological data contains a number of days of data related to the wearer's participation in exercise; and
update an exercise model using the retrieved physiological data.

6. The wearable drug delivery device of claim 5, wherein the processor, when evaluating the received data related to the wearer participating in exercise, is further operable to:
input values obtained from the received data in the exercise model; and
analyze an output of the exercise model with reference to threshold values related to exercise safety for the wearer.

7. The wearable drug delivery device of claim 1, wherein the received data includes a current blood glucose measurement value, a total daily insulin value, a time and amount of a requested bolus, a current insulin onboard value, or an amount of insulin delivered within a past evaluation period.

8. The wearable drug delivery device of claim 7, wherein the past evaluation period is a 15 minute period, a 30 minute period, a 60 minute period or a 120 minute period of time.

9. The wearable drug delivery device of claim 1, further comprising:
a communication device, wherein the communication device is operable to provide a wireless communication connection with an external device; and
the processor is further operable to:
control the communication device;
establish the wireless communication connection with the external device,
wherein the external device is a data network device;
retrieve physiological data from a memory source, wherein the physiological data contains a number of days of data related to the wearer's participation in exercise; and
update an exercise model using the retrieved physiological data.

10. The wearable drug delivery device of claim 1, wherein the processor is further configured to:
obtain data from a dataset including physiological data related to physiological conditions of the wearer;
split data in the dataset into training data and validation data;
train a logistic regression model using the training data;
use the validation data to validate an output of the logistic regression model;
based on a result of the validation of the output of the logistic regression model, perform hyperparameter tuning to improve accuracy of the logistic regression model;
retrieve the obtained data related to the physiological conditions of the wearer;
input the retrieved data into the logistic regression model for evaluation;
based on a value of output data from the logistic regression model, label the output data as either indicating an unsafe condition for exercise or a safe condition for exercise; and
generate the exercise safety signal based on any label indicating the unsafe condition for exercise.

11. The wearable drug delivery device of claim 1, further comprising:
an output device coupled to the processor, wherein the processor is further operable to:
interpret the outputted exercise safety signal; and
provide an output signal to the output device based on the outputted exercise safety signal.

12. The wearable drug delivery device of claim 1, wherein the processor is further operable to:
modify a medication treatment plan based on the outputted exercise safety signal.

13. A wearable drug delivery system, comprising:
a drug delivery device, including:
logic circuitry operable to control the drug delivery device;
a reservoir configured to contain insulin;
a communication device coupled to the logic circuitry; and
a pump mechanism responsive to the logic circuitry and fluidically coupled to the reservoir; and
a controller, including:
a processor;
a memory coupled to the processor and configured to store a medication delivery application, an exercise safety application, and programming code that, when the exercise safety application is executed by the processor, the processor is operable to:
receive an input related to a physiological condition of a wearer, wherein the input is from the wearer;
evaluate data parameters related to physiological conditions of a wearer and the received input related to the physiological condition of a wearer;
determine whether the wearer has participated in exercise;
in response to a determination that the wearer has participated in exercise and a result of the evaluation of the data parameters, generate an exercise safety signal;
present an indication of a result of an interpretation of the exercise safety signal, wherein the indication is a safe or unsafe indicator;
modify a medication treatment plan in response to the generation of the exercise safety signal, wherein the modifying includes lengthening an insulin on board (IOB) curve and using the lengthened IOB curve to determine basal insulin doses for a period of multiple hours.

14. The wearable drug delivery system of claim 13, wherein the data parameters related to physiological conditions of a wearer include one or more of:
a blood glucose measurement value,
a total daily insulin amount,
a request for a bolus,
a request to use a hypoglycemia protect mode,
a current calculation of an amount of insulin onboard, or an amount of insulin delivered in a past evaluation period.

15. The wearable drug delivery system of claim 13, wherein the controller is a device separate from the drug delivery device.

16. The wearable drug delivery system of claim 13, wherein the controller further comprises:
a user interface communicatively coupled to the processor and operable to receive the input related to a physiological condition of a wearer and provide the input to the processor, wherein the input is a request for a bolus dosage.

17. The wearable drug delivery system of claim 13, further comprising:

an analyte sensor configured to be attached to a body of the wearer, and including an analyte processor and an analyte communication device, wherein the analyte sensor is operable to:
measure a blood glucose measurement value of the wearer, and
communicate with the controller and the drug delivery device via the analyte communication device under control of the analyte processor.

18. The wearable drug delivery system of claim 13, wherein the processor, when evaluating the data parameters, is further operable to:
input data parameters including a blood glucose measurement value, a total daily insulin value, a time and an amount of a requested bolus, an amount of insulin onboard value, or an amount of insulin delivered within a past evaluation period into an exercise model; and
based on a result of an output from the exercise model, generate the exercise safety signal.

19. A non-transitory computer-readable storage medium, the computer-readable storage medium including instructions that when executed by a processor, cause the processor to:
determine that wearer of a wearable drug delivery device is participating in exercise;
lengthen an insulin on board curve in response to the determination that a wearer is participating in exercise;
use the lengthened insulin on board curve to calculate subsequent doses of insulin to be delivered to the wearer during a period of multiple hours.

20. The non-transitory computer-readable storage medium of claim 19, further including instructions that when executed by the processor, cause the processor to:
in response to the determination that the wearer of a wearable drug delivery device is participating in exercise, determine a current insulin onboard of the wearer;
compare the determined current insulin onboard to a threshold value set for the wearer;
in response to the current insulin onboard being above the threshold value set for the wearer, generate an exercise safety signal indicating an unsafe exercise condition; and
based on the generated exercise safety signal, suspend delivery of insulin for a period of time.

* * * * *